United States Patent
Dai et al.

(10) Patent No.: US 11,364,267 B1
(45) Date of Patent: Jun. 21, 2022

(54) BI-SPECIFIC TARGETING HUMAN NKG2DL AND CLDN18A2 CHIMERIC ANTIGEN RECEPTOR CELLS, PREPARATION METHOD AND APPLICATION THEREOF

(71) Applicant: NANJING KAEDI BIOTHERAPEUTICS LTD., Nanjing (CN)

(72) Inventors: Hongjiu Dai, Nanjing (CN); Hui Xu, Nanjing (CN); Jingjing Zhu, Nanjing (CN)

(73) Assignee: NANJING KAEDI BIOTHERAPEUTICS LTD., Nanjing (CN)

( * ) Notice: Subject to any disclaimer, the term of this patent is extended or adjusted under 35 U.S.C. 154(b) by 0 days.

(21) Appl. No.: 17/551,147

(22) Filed: Dec. 14, 2021

(51) Int. Cl.
| | |
|---|---|
| *A61K 35/17* | (2015.01) |
| *C12N 15/86* | (2006.01) |
| *C07K 16/28* | (2006.01) |
| *C07K 14/725* | (2006.01) |
| *A61P 35/00* | (2006.01) |

(52) U.S. Cl.
CPC .............. *A61K 35/17* (2013.01); *A61P 35/00* (2018.01); *C07K 14/7051* (2013.01); *C07K 16/2803* (2013.01); *C12N 15/86* (2013.01)

(58) Field of Classification Search
CPC ................ A61K 35/17; C07K 16/2803; C07K 14/7051; A61P 35/00; C12N 15/86
See application file for complete search history.

(56) References Cited

PUBLICATIONS

Ugur Sahin, et al., Claudin-18 Splice Variant 2 Is a Pan-Cancer Target Suitable for Therapeutic Antibody Development, Clinical Cancer Research, 2008, pp. 7624-7634, vol. 14, No. 23.

*Primary Examiner* — Ruixiang Li
(74) *Attorney, Agent, or Firm* — Bayramoglu Law Offices LLC

(57) ABSTRACT

A chimeric antigen receptor (CAR) cell bi-specifically targeting human NKG2DL and CLDN18A2, a preparation method and an application thereof are provided. The CAR includes a targeting human NKG2DL antigen domain, an anti-CLDN18A2 antigen binding domain, a hinge domain, a transmembrane domain, and an intracellular T cell signaling domain. Also provided are nucleic acids, recombinant expression vectors, immune effector cells, and a pharmaceutical composition relating to the CAR. The CAR can be used in methods of detecting the presence of cancer in a mammal and methods of treating or preventing cancer in a mammal.

7 Claims, 11 Drawing Sheets
Specification includes a Sequence Listing.

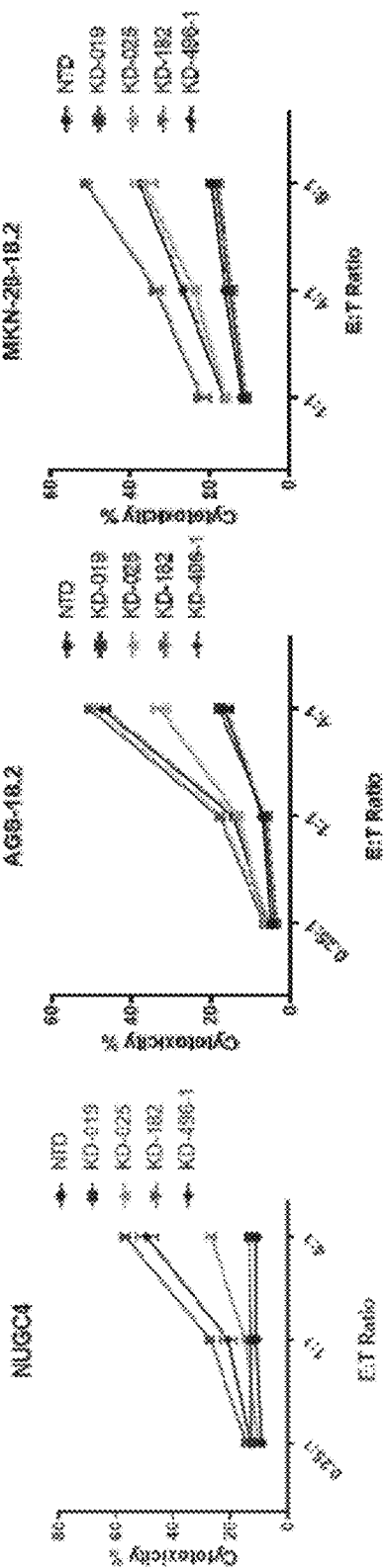
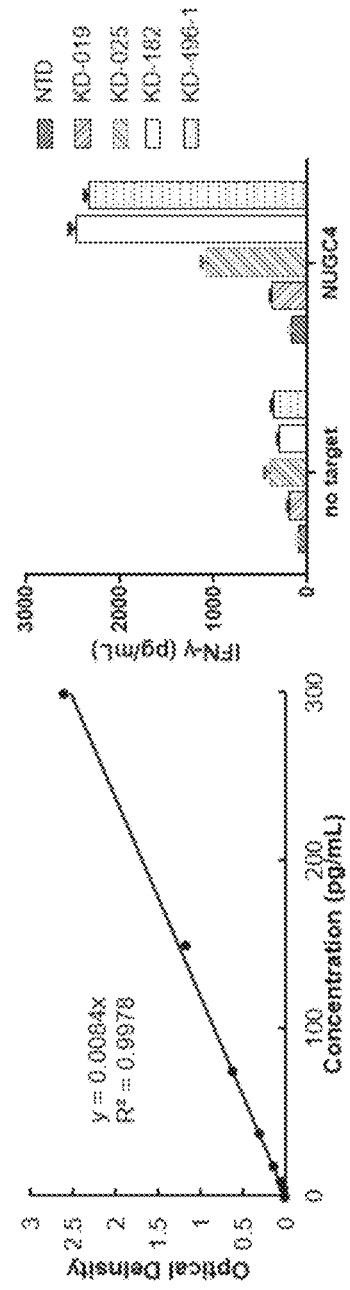
FIG. 7A  FIG. 7B  FIG. 7C
FIG. 8A  FIG. 8B

BI-SPECIFIC TARGETING HUMAN NKG2DL AND CLDN18A2 CHIMERIC ANTIGEN RECEPTOR CELLS, PREPARATION METHOD AND APPLICATION THEREOF

SEQUENCE LISTING

The instant application contains a Sequence Listing which has been submitted in ASCII format via EFS-Web and is hereby incorporated by reference in its entirety. The ASCII copy is named GBKDYL003_Sequence_Listing.txt, created on 12/05/2021 and is 37,483 bytes in size.

TECHNICAL FIELD

The invention belongs to the field of cell therapy for tumors, and particularly relates to an immune effector cell targeting NKG2DL and CLDN18A2, the preparation method and the application thereof.

BACKGROUND

With the rapid development of biotechnology, immune cell therapy has become the fourth major therapy in the field of cancer treatment.

Cancer immunotherapy mainly comprises adoptive cell therapy, immunomodulator, tumor vaccine and immunoassay, immunology checkpoint block therapy and so on. Among them, in the field of cell therapy, chimeric antigen receptor modified immune cell therapy, especially Chimeric Antigen Receptor T-Cell (CAR-T) therapy, has undoubtedly become a superstar for research institution and pharmaceutical industry.

CAR-T (Chimeric Antigen Receptor T-Cell, chimeric antigen receptor modified T cells) was used as a substitute. The principle of immune therapy is to modify T cells from the patients themselves by means of genetic engineering. The antigen receptor is modified to generate CAR-T cells, which can specifically recognize tumor surface associated antigens. The engineering of T cells can specifically recognize tumor surface antigen (tumor cell marker), thus targeting of the tumor. Relative to conventional immune cells, CAR-T cells has higher targeting, killing activity and persistence, and can overcome the local immunosuppressive microenvironment of tumor. And the state of host immune tolerance is broken. The modified immune cell therapy represented by CAR-T cells is urgent. The treatment of leukemia and non-Hodgkin's lymphoma has a significant progress and is regarded as the most promising therapy approach.

In recent years, studies have shown that the expression of NKG2DL protein is an indicator of the cell's "stress state". They are rarely expressed or expressed only in a short time in healthy tissues, but are usually found in different sources of cell surface has a high level of expression, such as myeloma cells and more than 80% of primary ovarian cancer cells. The expression of NKG2DL was found to indicate, especially the low dosage of chemotherapeutic drugs and radiotherapy, DNA damage of tumor cells and activation of DNA repair pathway, and the increased expression of NKG2DL was found on the surface of tumor cells. The receptor of NKG2DL protein is NKG2D. Research shows that NKG2D-NKG2DL system is on the machine, where the body plays an important role in anti-tumor immunity. NKG2D identifies NKG2DL on the surface of tumor cells. NKG2DL transmits activation signals and activates the immune system, thereby killing tumor cells. NKG2DLs expression are a specific change of tumor cells when the tumor occurs. This treatment provides a more precise target and inspiration for the development of new therapies and drugs.

In addition, some studies have shown that claudin, a tight junction protein, is a tetra-transmembrane protein. Both —NH$_2$ terminal and —COOH terminal are located in the cell and have two extracellular rings. So far, a total of 27 claudin family members have been found. CLDN18A2 is a tetra-transmembrane protein expressed at the epithelial tight junction in the claudin family. It is an important molecule of cell tight junction. It constitutes a paracellular barrier and controls the flow of molecules between cells. CLDN18A2 is a highly specific cell surface molecule, which is only expressed on differentiated gastric mucosal epithelial cells in normal tissues, so that the development of therapeutic antibodies against CLDN18A2 has greater anticancer potential, lower toxicity and greater space for optimal dosage. CLDN18A2 protein is highly expressed in solid tumors such as gastric cancer, pancreatic cancer, ovarian cancer, cholangiocarcinoma and lung adenocarcinoma (Sahin et al., Clinical Cancer Research (2008)). In addition, according to experts, tumors with high expression of CLDN18A2 often do not express PD-L1 and are not sensitive to immunosuppressive drugs targeted by PD-L1. Therefore, it is a field with high unmet clinical needs. The unique expression profile of CLDN18A2 in normal tissues and its abnormal expression in a variety of tumors make it a very attractive target for anticancer therapy. At the same time, the exposed extracellular structure of CLDN18A2 allows for antibody binding, which makes it an ideal therapeutic target. Thus, CLDN18A2 is an ideal tumor antigen target of immunotherapy.

In summary, the inventors constructed a new type of highly specific immune response cells modified by the activated targets NKG2DL and CLDN18A2, and their mutant peptides based on CLDN18A2-NKG2DL system as bi-specific chimeric antigen receptors targeting tumor regions for tumor treatment.

SUMMARY

An embodiment of the invention provides a bi-specific chimeric antigen receptor (CAR) targeting human NKG2DL and CLDN18A2, the CAR comprising a targeting human NKG2DL antigen domain, an anti-CLDN18A2 antigen binding domain, a hinge domain, a transmembrane domain, and an intracellular T cell signaling domain.

Further embodiments of the invention provide related nucleic acids, recombinant expression vectors, immune effector cells, and pharmaceutical relating to the CARs of the invention.

Additional embodiments of the invention provide methods of detecting the presence of cancer in a mammal and methods of treating or preventing cancer in a mammal.

The purpose of the present invention is to provide an immune effector cell targeting human NKG2DL and CLDN18A2 and the preparation method and application thereof.

In the first aspect, the invention provides a chimeric antigen receptor that bi-specifically targets human NKG2DL and CLDN18A2.

In some embodiments, the amino acid sequence of the targeted human CLDN18A2 is the amino acid sequence shown in SEQ ID NO: 2, SEQ ID NO: 3, SEQ ID NO: 4 or SEQ ID NO: 5; or a variant produced by amino acid modification with 80-99% homology to any one amino acid sequence of SEQ ID NOS: 2-5.

In some embodiments, the human NKG2D protein receptor targeting human NKG2DL or its functional variant (Analog), which comprises a sequence selected from the following group: the amino acid sequence shown in SEQ ID NO: 6, SEQ ID NO: 7, SEQ ID NO: 8, SEQ ID NO: 9, SEQ ID NO: 10 or SEQ ID NO: 11, or the functional variant produced by amino acid modification at one or more places; wherein the amino acid modified functional variant is a polypeptide with 80-99% homology with any one amino acid sequence shown in SEQ ID NOS: 6-11.

The inventor through creative work continuously carried out amino acid sequence design, sequence arrangement, combination and screening, random screening test and targeted function verification on the sequences of more than tens of CAR molecules (such as constructing virus vector, further infecting T cells, obtaining modified T cells, and detecting the in vitro activity of the modified T cells). Then, according to the results of multiple random combinations, sequence optimization was carried out and finally the sequence with the best effect was selected to verified the affinity the amino acid sequence and functional variant of human NKG2D protein receptor with high affinity.

After creative work, the inventor continuously performed amino acid sequence design, sequence arrangement, combination and screening, analyzed its biological characteristics with software, and selected the amino acid sequence and functional variant of high-efficiency valence CLDN18A2 with good stability and high affinity.

In some non-limiting embodiments, the chimeric antigen receptor that bi-specifically targets human NKG2DL and CLDN18A2 may also include a structure with the connecting amino acid sequence represented by formula $(G_4S)_n$, where $3 \leq n \leq 8$.

In the second aspect, the application provides a chimeric antigen receptor targeting human NKG2DL and CLDN18A2, which comprises an amino acid sequence of a guide sequence sequentially connected from the amino end to the carboxyl end, an amino acid sequence of human NKG2D, an amino acid sequence of protein specifically recognizing human CLDN18A2, an amino acid sequence of a hinge region, an amino acid sequence of the transmembrane domain, and an amino acid sequence of the intracellular signal domain. The amino acid sequence targeting the extracellular recognition domain of human NKG2DL comprises the human NKG2D protein receptor targeting human NKG2DL or a functional variant thereof described in the first aspect of the invention. In addition, the amino acid sequence of protein specifically recognizing human CLDN18A2 described in the first aspect of the application.

In some non-limiting embodiments, the leading sequence is covalently linked to the 5' end of the extracellular antigen binding domain.

In some embodiments, the chimeric antigen receptor that bi-specifically targets human NKG2DL and CLDN18A2 includes a hinge region.

In some embodiments, the transmembrane domain includes a transmembrane region.

In some embodiments, the amino acid sequence of the human CD8 polypeptide in the hinge region is selected from the polypeptide shown in SEQ ID NO: 12 or the amino acid modified functional variant, wherein the amino acid modified functional variant is a polypeptide with 90-99% homology with the amino acid sequence shown in SEQ ID NO: 12.

In some embodiments, the amino acid sequence of human CD8 in the transmembrane region is selected from the polypeptide shown in SEQ ID NO: 13 or the amino acid modified functional variant, wherein the amino acid modified functional variant is a polypeptide with 90-99% homology with the amino acid sequence shown in SEQ ID NO: 13.

In some embodiments, the amino acid sequence of human CD28 in the transmembrane region is selected from the polypeptide shown in SEQ ID NO: 14 or the amino acid modified functional variant, wherein the amino acid modified functional variant is a polypeptide with 90-99% homology with the amino acid sequence shown in SEQ ID NO: 14.

In some embodiments, the human 4-1BB intracellular domain is selected from: a polypeptide having an amino acid sequence as shown in SEQ ID NO: 15; or an amino acid modified functional variant, wherein the amino acid modified functional variant is a polypeptide with 90-99% homology with the amino acid sequence shown in SEQ ID NO: 15.

In some embodiments, the human CD28 intracellular domain is selected from: a polypeptide having an amino acid sequence as shown in SEQ ID NO: 16; or an amino acid modified functional variant, wherein the amino acid modified functional variant is a polypeptide with 90-99% homology with the amino acid sequence shown in SEQ ID NO: 16.

In some embodiments, the human OX40 intracellular domain is selected from: a polypeptide having an amino acid sequence as shown in SEQ ID NO: 17; or an amino acid modified functional variant, wherein the amino acid modified functional variant is a polypeptide with 90-99% homology with the amino acid sequence shown in SEQ ID NO: 17.

In some embodiments, the CD3 zeta intracellular domain is selected from: polypeptide with amino acid sequence as shown in SEQ ID NO: 18; or functional variants modified by amino acids. Wherein the amino acid modified functional variant is a polypeptide with 90-99% homology with the amino acid sequence shown in SEQ ID NO: 18.

In some non-limiting embodiments, the intracellular signal domain includes an immune receptor tyrosine activation motif and a costimulatory signal domain.

In some non-limiting embodiments, chimeric antigen receptors that bi-specifically target human NKG2DL and CLDN18A2 are recombinant or expressed by vectors.

In some non-limiting embodiments, the intracellular domain of the chimeric antigen receptor bi-specifically targeting human NKG2DL and CLDN18A2 of the invention also includes at least one costimulatory signal transduction region, which includes at least one costimulatory ligand molecule that can provide optimal lymphocyte activation.

In some non-limiting embodiments, chimeric antigen receptors that bi-specifically target human NKG2DL and CLDN18A2 may also include spacers that connect antigen binding domains to transmembrane domains. The spacer region can be flexible enough to allow the antigen binding domain to be oriented in different directions to facilitate antigen recognition. The spacer region may be a hinge region from IgG1, or a portion of CH2CH3 region and CD3 of immunoglobulin.

In some non-limiting embodiments, the intracellular domain of chimeric antigen receptors that bi-specifically targeting human NKG2DL and CLDN18A2 may include human CD3 that can activate or stimulate cells (e.g., T cells of the lymphatic lineage) zeta Polypeptide.

In some non-limiting embodiments, the intracellular domain of the chimeric antigen receptor (CAR) bi-specifically targeting human NKG2DL and CLDN18A2 also includes at least one costimulatory signal transduction region, which includes at least one costimulatory molecule that provides optimal lymphocyte activation. At least one costimulatory signal transduction region may comprise a CD28 polypeptide, a 4-1BB polypeptide, an OX40 polypeptide, an ICOS polypeptide (not based on proteins related to the immune response), or a combination thereof.

In some embodiments, the costimulatory signal transduction region of the intracellular domain of CAR contains two costimulatory molecules such as CD28 and 4-1BB, 4-1BB and OX40 or CD28 and OX40.

In the third aspect, the application provides a nucleic acid molecule encoding the chimeric antigen receptor of human NKG2DL and CLDN18A2 described in the second aspect. The nucleic acids molecule of the invention may comprise a nucleotide sequence encoding a leader sequence, an anti-human CLDN18A2 antigen binding domain, a targeting human NKG2DL binding domain, a hinge and transmembrane domain, linkers, and/or intracellular signaling domains described herein.

In some embodiments, the nucleic acid molecule also comprises a nucleotide sequence encoding a hinge region.

In some embodiments, the intracellular signal domain includes an immune receptor tyrosine activation motif and a costimulatory signal domain.

In the fourth aspect, the application provides a recombinant vector or expression plasmid comprising a chimeric antigen receptor of the second aspect of the application or a nucleic acid of the third aspect of the application.

In some embodiments, gene modification of immune response cells (e.g., T cells, CTL cells, NK cells) can be achieved by transduction of substantially homologous cell compositions with recombinant DNA or RNA constructs. In one embodiment, the vector is a retroviral vector (for example, γ Retrovirus or lentivirus), which can introduce DNA or RNA constructs into the host cell genome. For example, polynucleotides bi-specifically targeting chimeric antigen receptors of human NKG2DL and CLDN18A2 can be cloned into retroviral vectors and can be driven for expression from their endogenous promoters, retroviral long terminal repeats, or alternative internal promoters.

In some embodiments, nonviral vectors or RNA may also be used. Random chromosome integration or targeted integration can be used (e.g., using nucleases, transcription activator like effector nucleases (TATEN), zinc finger nucleases (ZFN), and/or regularly clustered short palindrome repeats (CRISPR) or transgene expression (e.g., using naturally or chemically modified RNA)).

In some embodiments, the carrier is selected from γ-Retroviral vector, lentiviral vector, adenovirus vector, and adenovirus vector.

In a preferable embodiment, the carrier is γ-Retroviral vector.

In the fifth aspect, the invention provides a recombinant virus, which is a virus capable of expressing a chimeric antigen receptor that bi-specifically targets human NKG2DL and CLDN18A2 as described in the second aspect of the present invention and can infect immune response cells.

In some embodiments, the immune response cells are cytotoxic T lymphocytes, NK cells, NKT cells, helper T cells or macrophages.

In a preferable embodiment, the immune response cells are cytotoxic T lymphocytes.

In some embodiments, the virus is a lentivirus, an adenovirus, an adeno-associated virus, a retrovirus, or the like.

In a preferable embodiment, the virus is a lentivirus.

In a preferable embodiment, the virus is a retrovirus.

In the sixth aspect, the application provides a modified immune response cell, which comprises the chimeric antigen receptor described in the second aspect of the application, and it is transformed by the recombinant vector or expression plasmid described in the fourth aspect of the application and by the recombinant virus described in the fifth aspect of the application.

For the initial genetic modification of cells to provide the chimeric antigen receptor modified immune response cells that bi-specifically target human NKG2DL and CLDN18A2, retroviral vectors are usually used for transduction, but any other suitable viral vectors or non-viral delivery systems can be used. Retroviral gene transfer (transduction) has also proved effective for subsequent genetic modification of cells to provide cells containing antigen-presenting complexes containing at least two costimulatory ligands. The combination of retroviral vector and appropriate assembly line is also appropriate, in which capsid protein is functional for infecting human cells.

In some embodiments, possible transduction methods also include direct co culture of cells with production cells. Transduced viral vectors can be used to express costimulatory ligands (e.g., 4-1BBL) in immune response cells. Preferably, the selected vector exhibits high infection efficiency and stable integration and expression.

In some embodiments, preferably, the at least one costimulatory ligand is selected from 4-1BBL, CD80, CD86, CD70, OX40L, CD48, TNFRSF14 and combinations thereof, or more preferably, the costimulatory ligand is 4-1BBL.

In some embodiments, the immune response cells are selected from T cells, natural killer (NK) cells, cytotoxic T lymphocytes (CTLs), regulatory T cells, macrophages, human embryonic stem cells and pluripotent stem cells that can differentiate into lymphoid cells, preferably T cells and natural killer (NK) cells, more preferably T cells.

Multiple T cell subsets isolated from patients can be transduced using vectors for car expression.

In a preferable embodiment, the modified immune response cells are CAR-T cells. Genetically modified central memory T cells can be prepared by using the chimeric antigen receptors targeting human NKG2DL and CLDN18A2, and then stored in cold storage.

In the seventh aspect, the invention provides a preparation method of the chimeric antigen receptor modified immune response cell in the sixth aspect of the invention, comprising the following steps:

Firstly, the nucleic acid molecule described in the third aspect is connected to the expression vector by molecular cloning to obtain the expression vector of the chimeric antigen receptor targeting human NKG2DL and CLDN18A2.

Then, the obtained chimeric antigen receptor expression vector targeting human NKG2DL and CLDN18A2 is transfected into 293T cells to obtain virus solution.

Finally, the immune response cells are infected with the virus solution, and the immune response cells modified by the chimeric antigen receptor expressing the bi-specific targeting human NKG2DL and CLDN18A2 are obtained from the infected cells.

In some non-limiting embodiments, the immune response cells modified by the present invention may be cells of the lymphatic lineage. The cells of the lymphatic lineage are selected from B cells, T cells and natural killer (NK) cells and provide the functions of antibody production, regulation of cellular immune system, detection of foreign substances in blood, detection of host foreign cells, etc. Non-limiting examples of cells of the lymphoid lineage include T cells, natural killer (NK) cells, cytotoxic T lymphocytes (CTLs), regulatory T cells, macrophages, embryonic stem cells, and pluripotent stem cells (e.g., pluripotent stem cells that can differentiate into lymphoid cells).

In some embodiments, the immune response cells are selected from T cells, natural killer (NK) cells, cytotoxic T lymphocytes (CTLs), regulatory T cells, macrophages, human embryonic stem cells and pluripotent stem cells that can differentiate into lymphoid cells, preferably T cells or natural killer (NK) cells.

In some preferably embodiments, T cells are lymphocytes that mature in the thymus and are primarily responsible for cell-mediated immunity. T cells are involved in the acquired immune system.

In some non-limiting embodiments, T cells include, but are not limited to, T helper cells, cytotoxic T cells, memory T cells (including central memory T cells, stem cell like memory T cells), and two types of effector memory T cells (e.g., TEM cells and TEMRA cells), regulatory T cells (also known as inhibitory T cells), natural killer T cells, mucosal associated constant T cells, and γδ T cells. In some embodiments, CAR expressing T cells express Foxp3 to achieve and maintain a T-regulated phenotype.

In some embodiments, at least one costimulatory ligand is selected from 4-1BBL, CD80, CD86, CD70, OX40L, and combinations thereof. In one embodiment, the costimulatory ligand is 4-1BBL.

In a preferred embodiment, the isolated modified immune response cells are T cells.

In a preferred embodiment, the isolated modified immune response cells are natural killer (NK) cells.

In some non-limiting embodiments, the isolated modified immune response cells (e.g., T cells) may be autologous, non-autologous (e.g., allogeneic), or derived from engineered progenitor cells or stem cells in vitro.

In an eighth aspect, the invention provides a pharmaceutical composition comprising an effective amount of modified immune response cells as described in the sixth aspect of the invention and a pharmaceutically acceptable excipient.

In some embodiments, the pharmaceutical composition disclosed in the invention comprises modified immune response cells expressing the chimeric antigen receptors that bi-specifically target human NKG2DL and CLDN18A2.

In some embodiments, the administration of the pharmaceutical composition can be autologous or allogenous. For example, the immune response cells expressing the chimeric antigen receptors targeting human NKG2DL and CLDN18A2 and the composition containing it can be obtained from one subject and applied to the same subject or different compatible subjects. It can be administered by including catheter administration, intravenous injection or parenteral injection. Administration to administer peripheral blood derived T cells or their offspring (e.g., in vivo, in vitro or in vitro derived) of the disclosed subject of the present invention. When administering a pharmaceutical composition of the disclosed subject of the present invention (e.g., a pharmaceutical composition comprising the immune response cells that bi-specifically target the chimeric antigen receptors of human NKG2DL and CLDN18A2), it is usually prepared in clinical administration form per unit dose (solution, suspension, emulsion).

In some embodiments, the composition of the invention can be a preparation. The invention discloses a chimeric antigen receptor (CAR) expressing the bi-specific targeting human NKG2DL and CLDN18A2. The immune response cells and the compositions containing them can be conveniently provided as aseptic liquid preparations, such as isotonic aqueous solutions, suspension, emulsion, dispersion or viscous composition.

Various additives can be added to enhance the stability and sterility of the composition, including antimicrobial preservatives, antioxidants, chelators and buffers.

According to the invention, any vector, diluent or additive used must be compatible with the immune response cells expressing the chimeric antigen receptor (CAR) that bi-specifically targets human NKG2DL and CLDN18A2.

If desired, the viscosity of the composition can be maintained at a selected level using a pharmaceutically acceptable thickener. The selection of suitable carriers and other additives will depend on the exact route of administration and the properties of specific dosage forms, such as liquid dosage forms (for example, whether the composition is made into solution, suspension or another liquid form, such as time release form or liquid filling form).

In a ninth aspect, the invention provides a kit for treating or preventing diseases, which comprises an immune response cell described in the sixth aspect of the present invention or a nucleic acid described in the third aspect of the present invention.

In the tenth aspect, the application provides the human NKG2D protein receptor or functional variant thereof that targets and binds human CLDN18A2 and human NKG2DL in the first aspect of the invention, the chimeric antigen receptor that bi-specifically targets human NKG2DL and CLDN18A2 in the second aspect, the recombinant vector or expression plasmid in the fourth aspect, the recombinant virus in the fifth aspect and the chimeric antigen receptor modified immune cells in the sixth aspect. The application of the kit described in the ninth aspect in the treatment or prevention of diseases, discomfort or health disorders.

In some embodiments, the treated or prevented diseases include anti-tumor, anti-aging, autoimmune diseases, anti-bacterial and other diseases.

Action Mechanism

The bi-specificity of the invention targets the chimeric antigen receptor modified immune response cells of human NKG2DL and CLDN18A2. The engineering cells transmit activation signals and activate the immune system by recognizing tumor cell surface antigens NKG2DL and CLDN18A2, so as to kill tumor cells (as shown in FIGS. 1A-1B). The bispecific chimeric antigen receptor modified immune response cells targeting NKG2DL and CLDN18A2 can improve the specific killing efficiency of tumor cells, avoid the safety problems of therapeutic toxicity caused by off target, and enhance the binding with tumor cells, thus providing a promising new method of tumor treatment.

Beneficial Effect

The invention uses the chimeric antigen receptor modified T cell technology to prepare chimeric antigen receptor modified engineered immune cells that bi-specifically target human NKG2DL and CLDN18A2. The preparation method has simple steps, and the obtained new engineered immune cells can specifically recognize tumor cells, more effectively target tumor cells and have high killing rate to tumors, it can also be used to prepare anti-tumor products, especially for the treatment of NKG2DL and CLDN18A2 positive tumors. The engineered immune cells modified specifically targeting human NKG2DL and CLDN18A2 chimeric antigen receptor enhance the binding with tumor cells, so as to significantly improve the killing efficiency of engineered immune cells to tumor cells. The invention can be used for preparing anti-tumor products, especially for preparing drugs for gastric cancer, pancreatic cancer, liver cancer, brain cancer, prostate cancer, prostate cancer, lymphatic cancer, leukemia, colon cancer, lung cancer, or breast cancer, and has good industrial application prospects.

BRIEF DESCRIPTION OF THE DRAWINGS

FIGS. 1A-1B show the schematic diagram of the KD-496 engineered cell of the invention, wherein FIG. 1A is CLDN18A2-NKG2D-CAR and FIG. 1B is NKG2D-CLDN 18.2-CAR.

FIG. 2A is KD-182 (CLDN18A2-CAR), FIG. 2B is KD-025 (NKG2D-CAR), and FIG. 2C is KD-496.

FIG. 3A is the secondary structure diagram of human NKG2D protein having the amino acid sequence of SEQ ID NO: 6; FIG. 3B is the secondary structure diagram of human NKG2D protein having the amino acid sequence of SEQ ID NO: 7; FIG. 3C is the secondary structure diagram of human NKG2D protein having the amino acid sequence of SEQ ID NO: 8; FIG. 3D is the secondary structure diagram of human NKG2D protein having the amino acid sequence of SEQ ID NO: 9; FIG. 3E is the secondary structure diagram of human NKG2D protein having the amino acid sequence of SEQ ID NO: 10; FIG. 3F is the secondary structure diagram of human NKG2D protein having the amino acid sequence of SEQ ID NO: 11.

FIG. 6A is the expression of NKG2D and anti-CLDN 18.2 scFv antibody. FIG. 6B is the binding ability of KD-496 CAR-T cells with the antigens.

FIGS. 7A-7C depict the cytotoxicity of KD-496-1 CAR-T cells on different target cells in vitro in embodiment 6, wherein FIG. 7A is NUGC4 cell, FIG. 7B is AGS-18.2 cell, and FIG. 7C is MKN28-18.2 cell.

FIGS. 8A-8B show the results of cytokine release in the supernatant by KD-496 CAR-T cells in vitro in embodiment 7, in which FIG. 8A is the standard curve of ELISA, and FIG. 8B is the column chart of IFN-γ release.

FIGS. 9A-9B depict KD-496-1 CAR-T cells antitumor activity in vivo in embodiment 8, wherein FIG. 9A is the antigen expression of human tumor tissue in PDX model, and FIG. 9B is the efficacy of KD-496-1 CAR-T cells in vivo.

FIGS. 10A-10B depict the on-target off-tumor toxicities of KD-496-1 CAR-T in mice in embodiment 9, wherein FIG. 10A is the HE staining of mouse organs, and FIG. 10B is the survival rate of mice.

DETAILED DESCRIPTION OF THE EMBODIMENTS

Figure 1A:
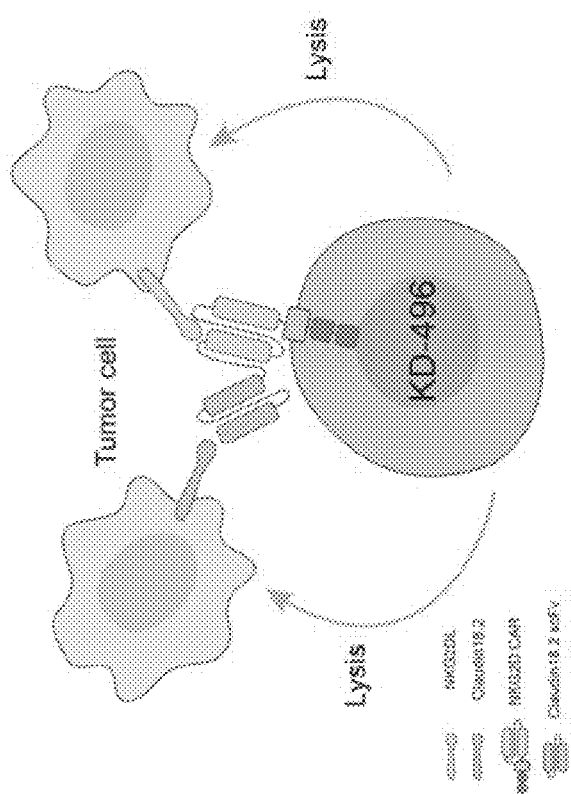
Figure 1B:
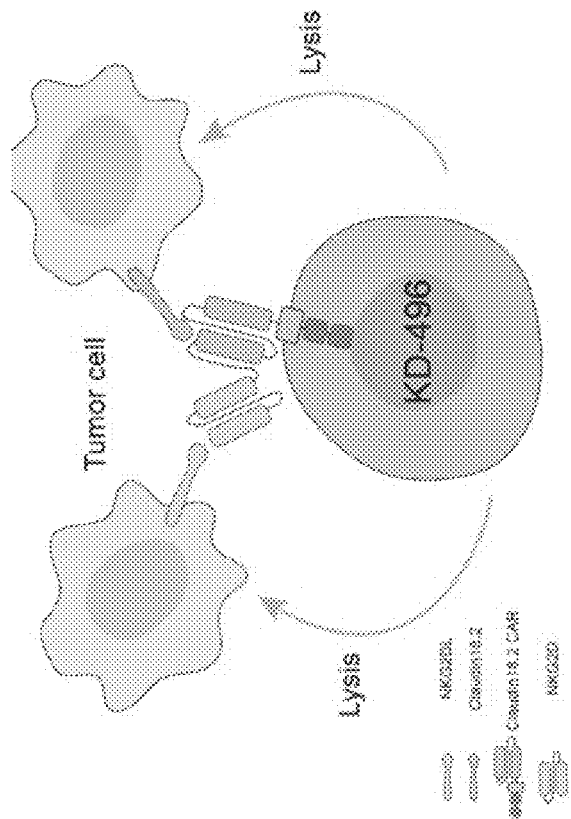

Unless otherwise defined, all technical and scientific terms used herein have meanings generally understood by those skilled in the art to which the invention belongs.

The term "functional variant" refers to the modified maternal structure. The term "functional variant" refers to the structural variant with the same or similar biological functions and properties as the mother, such as the same targeted binding function as the mother. As a non-limiting example, "functional variants" can be obtained by performing one or more conservative substitutions in the parent. The functional variant in this application is the structure combined with the human NKG2DL target modified on the basis of the human NKG2DL receptor (human NKG2D amino acid sequence), and the structure combined with the human CLDN18A2 target modified on the basis of the CLDN18A2 amino acid sequence.

The term "analog" refers to a structurally related polypeptide that has the function of referring to a polypeptide molecule. In the invention, it refers to a poly amino acid structure related to the amino acid sequence structure of human NKG2D and having targeted binding with human NKG2DL; and a poly amino acid structure related to the amino acid sequence structure of CLDN18A2 and targeted binding with human CLDN18A2.

The term "amino acid modification" refers to a conservative amino acid modification that does not significantly affect or change the binding characteristics of the car (e.g., extracellular recognition domain) of the present disclosure containing amino acid sequences. This conservative modification includes amino acid substitution, addition and deletion.

The term "conservative amino acid substitution" is a substitution in which an amino acid residue is replaced by an amino acid in the same group.

The term "homology" refers to the high proportion of amino acids or nucleotides shown by the comparison of the target amino sequence or target nucleotide sequence with the reference sequence. The homology in this application can be determined using standard software such as blast or FASTA.

The term "chimeric antigen receptor (CAR)": a chimeric antigen receptor includes a guiding peptide portion, an extracellular target recognition domain, a transmembrane domain, and an intracellular domain.

CAR can both bind antigen and transduce the function of T cell activation, which is independent of MHC restriction. Therefore, car is a "universal" immune antigen receptor, which can treat a population of patients with antigen positive tumors, regardless of their HLA genotype. Adoptive immunotherapy using T lymphocytes expressing tumor specific car can be a powerful therapeutic strategy for the treatment of cancer.

The term "single-chain fragment variable (scFv)" as used herein refers to an antibody fragment defined as follows. It is a recombinant protein comprising a light chain variable region (VL) and a heavy chain variable region (VH) connected by a linker, and the linker associates the two domains by which an antigen binding site is finally formed.

The term "identification" refers to selectively binding targets. The term "specific binding" or "specific binding to" or "specific targeting" as used herein refers to that a polypeptide or a fragment thereof recognizes and binds a target biomolecule (such as a polypeptide), but it basically does not recognize other molecules in the binding sample, such as other molecules in the biological sample naturally including the polypeptide of the invention.

The term "specific binding" refers to the binding between two molecules (such as ligands and receptors), which is characterized by the ability of one molecule (ligand) to bind to another specific molecule (receptor), that is, the ability to show the preferential binding of one molecule to another in a heterogeneous mixture of molecules. The specific binding of ligand to receptor was also proved as follows: when there were too many unlabeled ligands, the binding of detectable labeled ligand to receptor decreased (i.e., binding competition test).

The term "costimulatory molecules" refers to cell surface molecules other than antigen receptors or their ligands required for the effective response of lymphocytes to antigens.

The term "vector" refers to any genetic element, such as plasmid, phage, transposon, clay particle, chromosome, virus, virus particle, etc., which can replicate when associated with appropriate control elements, and which can transfer gene sequences into cells. Therefore, the term includes cloning and expression vectors, as well as viral vectors and plasmid vectors.

The term "expression vector" refers to a recombinant nucleic acid sequence, that is, a recombinant DNA molecule containing a desired coding sequence and an appropriate nucleic acid sequence necessary to express an operably linked coding sequence in a specific host organism. Nucleic acid sequences necessary for expression in prokaryotes usually include promoters, operons (optional) and ribosomal binding sites, usually accompanied by other sequences. Eukaryotic cells are known to use promoters, enhancers and terminators and polyadenylation signals.

The term "immune response cell" used herein refers to a cell that plays a role in the immune response, or its progenitor cells, or its progeny cells.

The term "isolated cells" refers to immune cells isolated from molecules and/or cellular components of natural companion cells.

The term "adjustment" as used herein refers to a positive or negative change.

The term "exogenous" as used herein refers to nucleic acid molecules or peptides that are not endogenous in cells or do not exist at a level sufficient to achieve the functional effects obtained when overexpressed. Therefore, the term "exogenous" will include any recombinant nucleic acid molecules or polypeptides expressed in cells, such as exogenous, allogenous and overexpressed nucleic acid molecules and polypeptides.

The term "exogenous nucleic acid molecule or polypeptide" used herein refers to nucleic acid molecules (e.g., cDNA, DNA or RNA molecules) or polypeptides that do not normally exist in cells or in samples obtained by cells. The nucleic acid may come from another organism, or it may be, for example, an mRNA molecule that is not normally expressed in a cell or sample.

The invention is further described below through embodiments, but the invention is not limited to these specific embodiments. The materials and reagents used in the following embodiments can be obtained from commercial sources unless otherwise specified.

EXAMPLES

The embodiments of the present invention are further described below with reference to specific examples, but the invention is not limited to the scope of the invention.

The materials and reagents used in the following embodiments can be acquired from commercial companies without special explanation.

Example 1. Construction of Lentiviral Plasmids (KD-496-1 and KD-496-2 Lentiviral Vectors) Expressing Chimeric Antigen Receptor Proteins Encoded by the Nucleic Acids of the Present Invention The overall design was as follows:

Firstly, by repeatedly researching and analyzing, the inventors identified several scFv antibodies recognizing human CLDN18A2 protein, and their amino acid sequences are shown as SEQ ID NOS: 2-5, and several NKG2D proteins recognizing human NKG2DL protein, and their amino acid sequences are shown as SEQ ID NOS: 6-11.

FIGS. 3A-3F are the characteristics of NKG2D and its ligand NKG2DL according to the extracellular region of the amino acid sequence of human NKG2D. That is, based on the crystal structure of the complex composed of NKG2D and its ligand NKG2DL (PDB No.: 4S0U). The inventor first obtains the amino acids at the key sites affecting affinity through alanine scanning, and then carries out saturation mutation of single point mutation. According to the results of the saturation mutation, the multi-point mutation was calculated, and the secondary structure diagrams of 6 sequences with good stability and high ligand binding affinity were selected.

Secondly, a chimeric antigen receptor bi-specifically targeting human NKG2DL and CLDN18A2 was constructed.

Figure 2A:
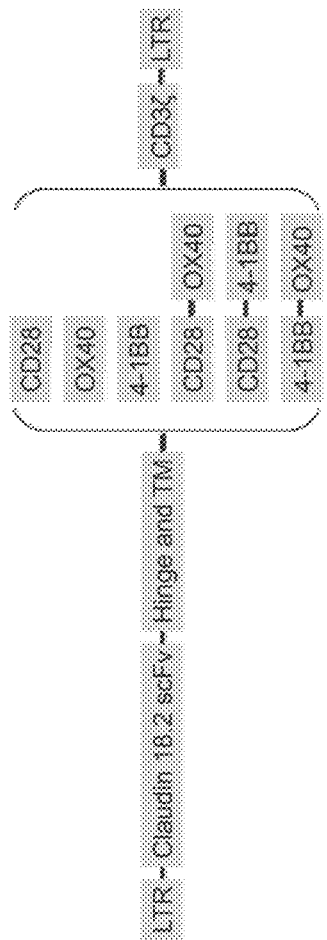
FIGS. 2A-2C are schematic diagrams of the connection sequence of each part of the chimeric antigen receptor in embodiment 1.
Figure 2B:
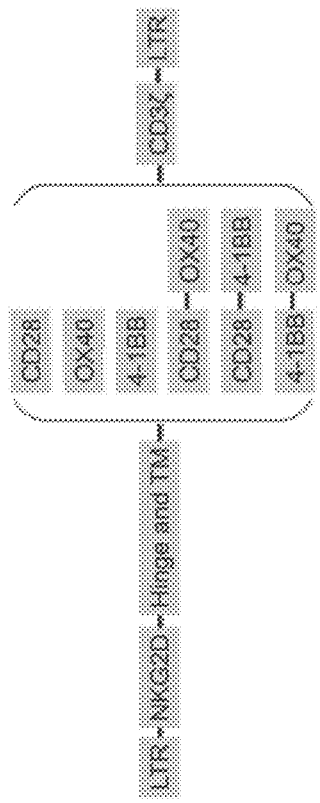
Figure 2C:
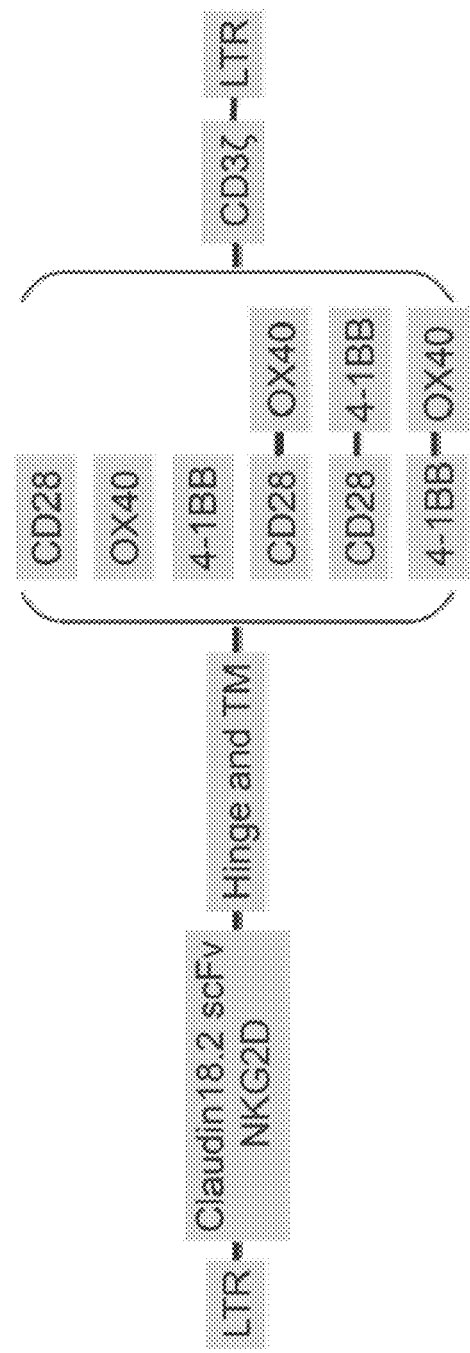
Figure 3A:
FIGS. 3A-3F show the secondary structure diagram of human NKG2D protein, the protein receptor targeting human NKG2DL in the chimeric antigen receptor of the invention.
Figure 3B:
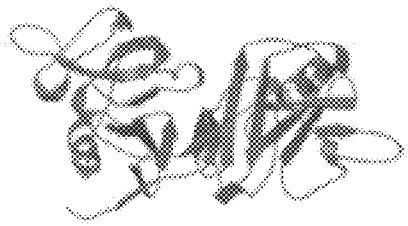
Figure 3C:
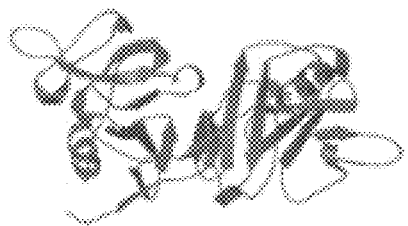
Figure 3D:
Figure 3E:
Figure 3F:

The corresponding nucleotide sequences comprise of scFv antibody recognizing human CLDN18A2, NKG2D extracellular domain, hinge region, transmembrane region, intracellular structure domain in series in turn (FIGS. 2A-2C).

Table 1 shows the vectors constructed by using different nucleotide sequences bi-specifically targeting human NKG2DL and CLDN18A2, and the corresponding CAR-T cells obtained according to the following methods. The results showed that there was no significant difference in CAR expression among the four groups, and one of the sequences were selected for subsequent efficacy verification.

TABLE 1

| Samples | Ammo acid sequence of CLDN18A2 single chain | Amino acid sequence of chimeric antigen receptor protein | CAR expression |
|---|---|---|---|
| KD-496-1 | SEQ ID NO: 2 | SEQ ID NO: 19 | 87.6% and 60.8% |
| KD-496-2 | SEQ ID NO: 3 | SEQ ID NO: 20 | 70.4% and 33.7% |

Thirdly, construction of lentiviral plasmids expressing chimeric antigen receptor molecule bi-specifically targeting human NKG2DL and CLDN18A2.

The invention selected four sequences in step 1, which are KD-496-1 (SEQ ID NO: 19), KD-4%-2 (SEQ ID NO: 20). From the amino end to the carboxyl end, by the guidance of peptide amino acid sequence (SEQ ID NO: 1). The selected sequences have amino acid sequence of protein specifically recognizing human CLDN18A2 (SEQ ID NOS: 2-3), amino acid sequence of human NKG2D (SEQ ID NO: 7), amino acid sequence of CD8 hinge region (SEQ ID NO: 12), amino acid sequence of human CD8 transmembrane area (SEQ ID NO: 13), 4-1BB intracellular structure domain of the amino acid sequence (SEQ ID NO: 15), and human CD3 zeta domain structure of amino acid sequence (SEQ ID NO: 18) in series in turn.

The whole gene synthesis specifically targeted the nucleotide sequence of the chimeric antigen receptor molecule of human CLDN18A2 and NKG2D (SEQ ID NOS: 21-22), and cloned into the lentiviral vector Lentigue-Purovia (Addgene, USA) to construct a full-length CAR sequence expression frame with a single coding frame, and an EF1a promoter was inserted in front of the CAR sequences.

The splicing conditions were as follows:

5 μL ligation product and 50 μL receptive cells (Stbl3, purchased from Invitrogen, USA) were added in a tube, incubated on ice for 30 min, 42° C. for 45 s, on ice for 2 min, then 500 μL non-anti-LB liquid medium was added, and shaken at 37° C., 200 rpm for 40 min. Finally, the suspension was coated on LB solid medium which has ampicillin, and the plates were incubated for 24 h at 37° C. When the single colony appearing, five moderately sized colonies were selected to extract plasmids and sent to the commercial company for sequencing. The right sequence will prove the plasmid expressing chimeric antigen receptor bi-specifically targeting human CLDN18A2 and NKG2D is obtained.

Extraction and purification of chimeric antigen receptor expressing plasmid (KD-496-1 and KD-496-2 lentiviral vectors) bi-specifically targeting human NKG2DL and CLDN18A2 by QIAGEN Plasmid Midi Kits (Qiagen AG, article No. 12143).

Example 2. Virus Packaging

Packaging lentivirus by plasmid transfection of HEK293T. The transfection steps were as follows: the lentiviral plasmids which express the chimeric antigen receptor bi-specifically targeting human NKG2DL and CLDN18A2 obtained from Example 1 were co-transfected into HEK293T cells with the packaging plasmids pMDLg/pRRE, pRSV-Rev and pMD2.G (Addgene, USA) at a specific ratio. Medium (purchased from Life Technologies) was replaced 6 hours after transfection, and the supernatant which are rich in virus particles are then collected after 48 hours and 72 hours respectively. Finally, a 0.45 μm filter (purchased from Millipore Company) was used to filter and collect the virus, and centrifuged at 25,000 rpm, 4° C. for 2 hours, and the centrifuged supernatant was discarded. The precipitate obtained by centrifugation was resuspended with stock solution which carries a lentiviral vector expressing a chimeric antigen receptor bi-specifically targeting human NKG2DL and CLDN18A2 (referred to as KD-496-1 and KD-496-2 lentivirus).

Example 3. Isolation and Culture of T Cells

Human peripheral blood mononuclear cells were obtained from healthy human peripheral blood through density gradient centrifugation method. T cells were obtained from peripheral blood mononuclear cells by negative sorting method with RosetteSep™ Human T Cell Enrichment Cocktail (purchased from Stem Cell Technologies), and the sorted cells were subjected to flow cytometry to determine the purity of the T cells.

Figure 4:
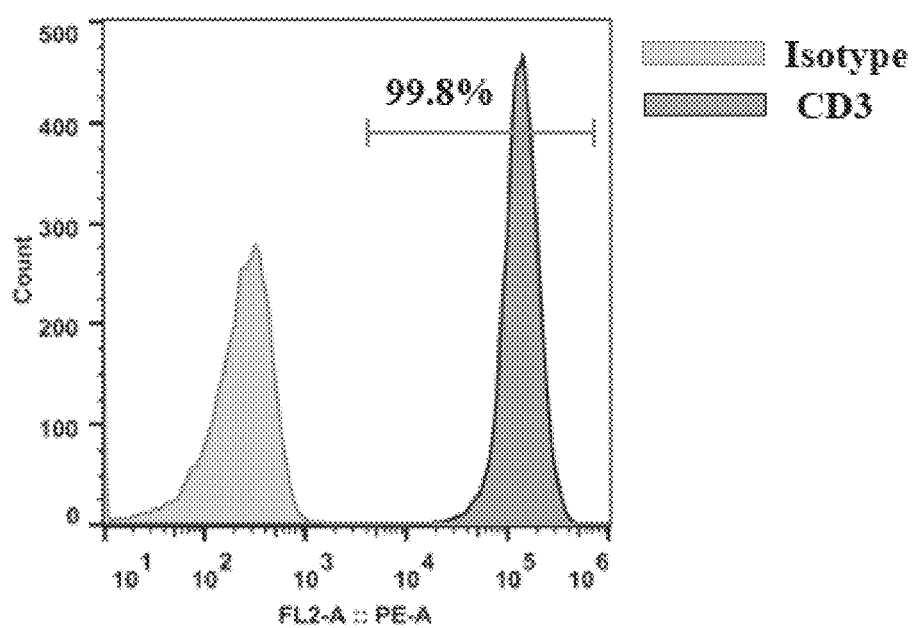
FIG. 4 is a flow cytometry result of T cell purity in embodiment 3.

Culture medium (purchased from Life Technologies) was added at a density of about $(1-3)\times 10^6$/ml for culturing, and magnetic beads (Invitrogen company) coated with both anti-CD3 and CD28 antibodies, at 3:1 cell-magnetic bead ratio, and recombinant human IL-2 with a final concentration of 100 U/ml were added to stimulate and culture for 48 h. As shown in FIG. 4, the purity of T cell was 99.8%.

Example 4. Recombinant Lentivirus Infection of T Cells

Figure 5:
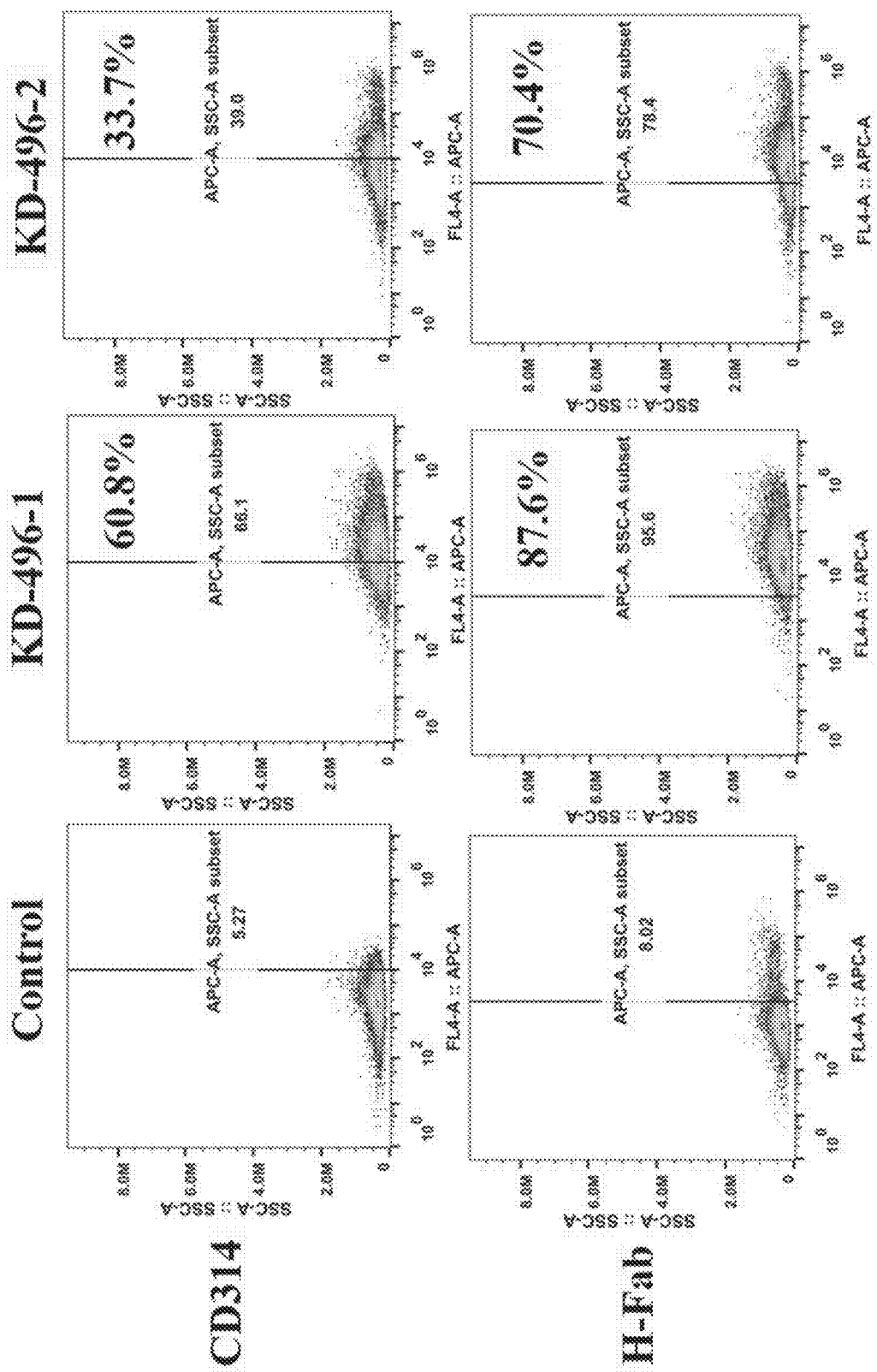
FIG. 5 shows the results of the expression of CAR molecules detected by flow cytometry in embodiment 4.

Firstly, CD3+ T cells obtained from Example 3 were inoculated into a 24-well plate at the inoculation concentration of $1\times 10^5$ cells/mL and incubated at 37° C., 5% $CO_2$ for 24 hours. Then the recombinant lentivirus from Example 2 were used to infect the T cells at MOI=1-10. After 48 hours, the control group was T cells infected with empty vector virus solution, and the expression of car molecule was almost undetectable. The experimental group was T cells infected with KD-496-1 and KD-496-2 virus solution. The expression rates of CLDN18A2 antibody scFv of KD-496-1 and KD-496-2 CAR-T cells were 87.6% and 70.4% respectively, and the expression rates of NKG2D were 60.8% and 33.7% respectively (FIG. 5 and Table 1).

Example 5: The Binding Ability of KD-496 with Antigens Such as MICA, ULBP2 and CLDN18A2 Proteins The specific operation steps were as follows:
Firstly, 293T cells (ATCC, USA) were inoculated into 24 well plates at a concentration of $1\text{-}10\times 10^5$ cells/mL were cultured at 37° C. and 5% $CO_2$ for about 24 hours (the culture time depends on the specific practice, the cell confluence rate is between 50-70% when the virus solution is infected). Then, infected 293T cells according to the value of MOI=10-40 by KD-496 virus solution were collected in example 2.

Figure 6A:
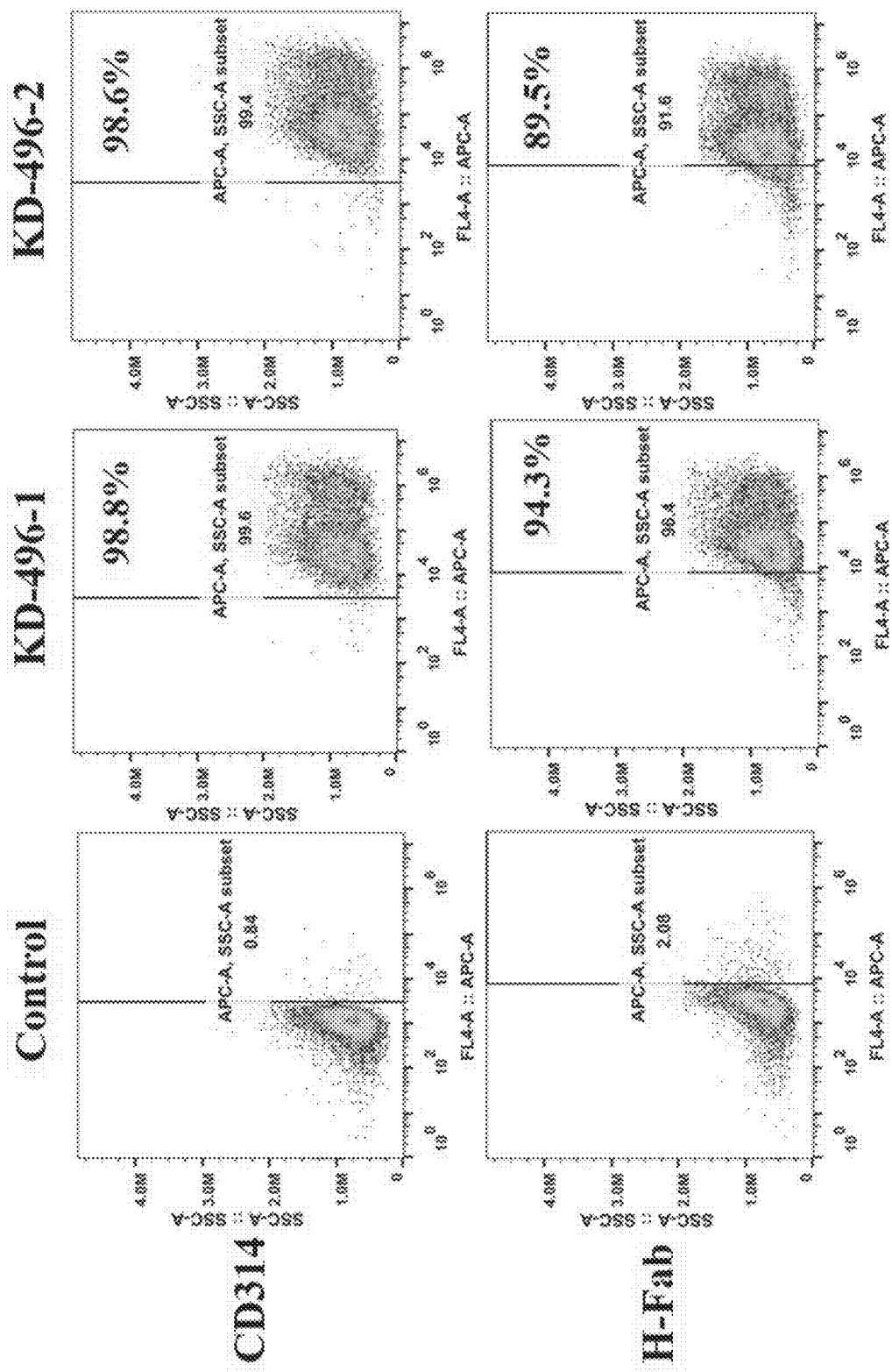
FIGS. 6A-6B depict the results of expression of KD-496 virus infected 293T cells in embodiment 5.
Figure 6B:
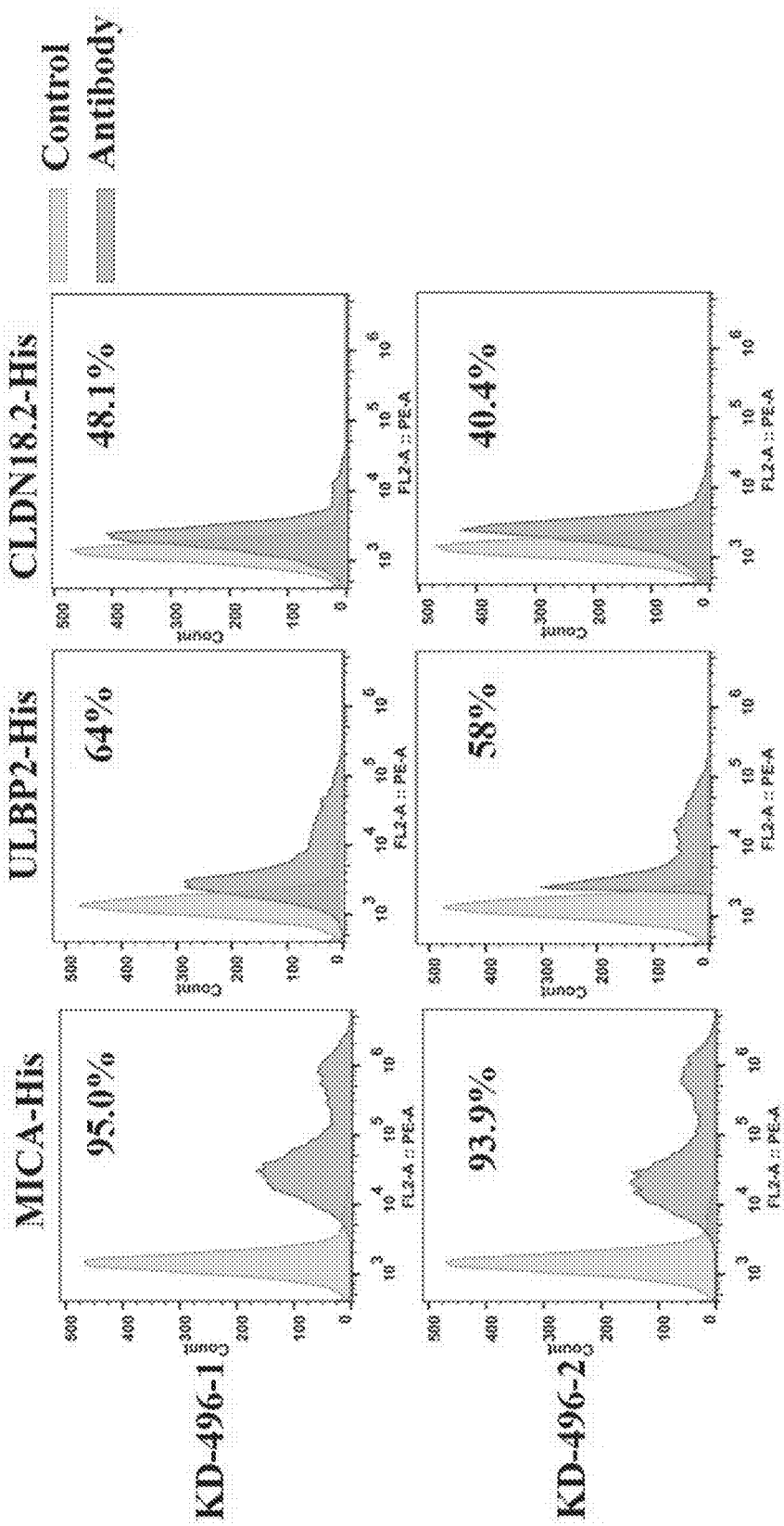

After 48 hours of culture, the cells were collected and centrifuged for 5 mm at 4° C.; after being washed twice with PBS, they were resuspended in FACS solution (PBS containing 0.1% sodium azide and 0.4% BSA); anti-CD314 antibody (APC anti human CD314 (NKG2D), biolegend, 320808) was added to the cell suspension, incubated at 4° C. for 1 h, and the same type control group (APC mouse IgG1, κ Isotype Ctrl antibody, biolegend, 400120). Add recombinant human MICA protein (mammalian, c-6his, C489), recombinant human ULBP2 protein (c-6his, C508) or recombinant human CLDN18A2 protein (CR53) into cell suspension respectively, incubate at 4° C. for 4 h, and set the control group; after cleaning cells twice, the cells were resuspended with 200 μL FACS solution; the secondary antibody was added to the cell suspension and incubated at 4° C. for 1 h in the dark; after cleaning the cells twice, the cells were resuspended with 200 μL FACS solution and detected by flow cytometry. The expression rates of anti-CLDN18A2 scFv antibody of KD-496-1 and KD-496-2 CAR-293T cells were 98.8% and 94.3% respectively, and the expression rates of NKG2D were 98.6% and 89.5% respectively (FIG. 6A). As shown in FIG. 6B, the control group was 293T cells that were not infected with virus solution, and almost did not bind to MICA, ULBP2 and CLDN18A2 proteins. The experimental group 293T cells infected with KD-496-1 and KD-496-2 virus solution had the binding rates of 95% and 93.9% with MICA protein, 64% and 58% with ULBP2 protein, 48.1% and 40.4% with CLDN18A2 protein.

Example 6. In Vitro Toxicity Effect Assay for KD-496-1 CAR-T Cells

Firstly, the effector cells (KD-019, KD-025, KD-182 and KD-496-1 CAR-T cells) were prepared according to the method of Example 4 and were inoculated 72 hours after infection. The antitumor activity of CAR-T cells was evaluated using a Cell-Mediated Cytotoxicity Fluorometric Assay Kit (BioVision, USA). Briefly, carboxyfluorescein succinimidyl ester (CFSE)-stained target cells were seeded into 96-wells at a density of $4\times 10^4$ cells/well. Subsequently, effector cells were added to each well to ensure an effector to target (E:T) ratios of 1:4, 1:1, and 4:1. After 24 h of co-culture, the tumor cells were collected, and dead cells were stained with 7-aminoactinomycin (7-AAD) and quantified by flow cytometry. KD-496-1 CAR-T cells could efficiently lyse NUGC-4, AGS-18.2 and MKN-28.2 cells. In contrast, CD19 CAR-T cells failed to initiate the specific lysis of these cell lines (FIGS. 7A-7C).

Example 7. Cytokine Secretion Assay for KD-496-1 CAR-T Cells

Firstly, the effector cells (KD-019, KD-025, KD-182 and KD-496-1 CAR-T cells) were prepared according to the method of Example 4 and were inoculated 72 hours after infection. The target cells were seeded into 96-wells at a density of $4 \times 10^4$ cells/well. Subsequently, effector cells were added to each well to ensure an effector to target (E:T) ratios of 5:1. After 24 h of co-culture, and the medium supernatant was assessed for the levels of cytokine secretion using Human IFN-γELISA Kit II (purchased from BD, No. 550612). As shown in FIGS. 8A-8B, greater amounts of IFN-γ were produced by both KD-182 and KD-496-1 CAR-T cells than the cells of control groups, and suggested that KD-496-1 CAR-T cells had a good anti-tumor effect.

Example 8. KD-496-1 CAR-T Cells Suppressed the Tumor Growth in Patient Derived Xenograft (PDX)

Figure 9A:
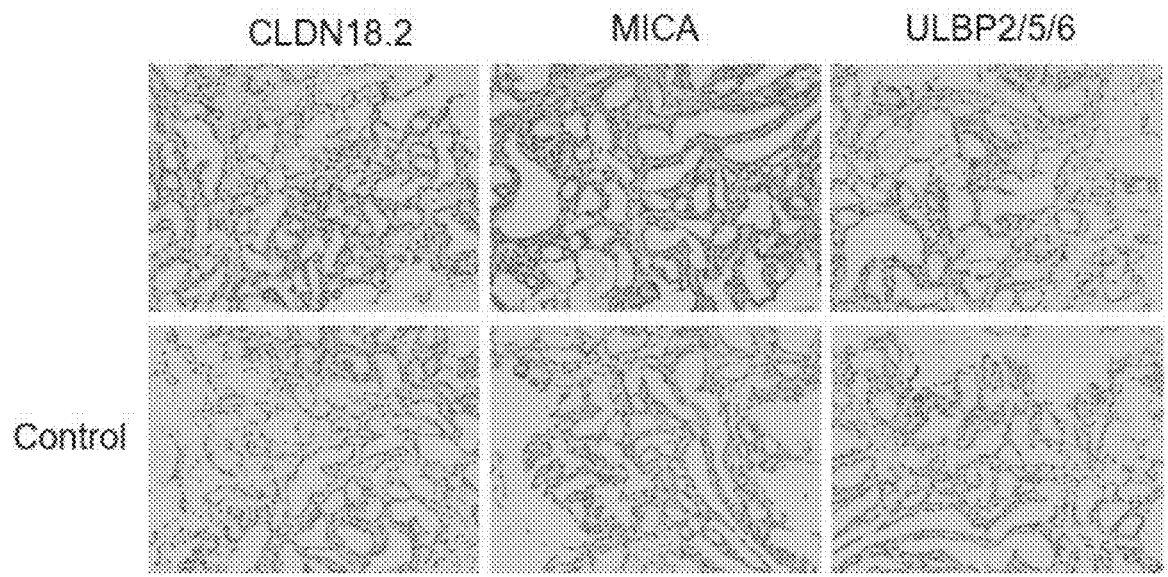
Figure 9B:
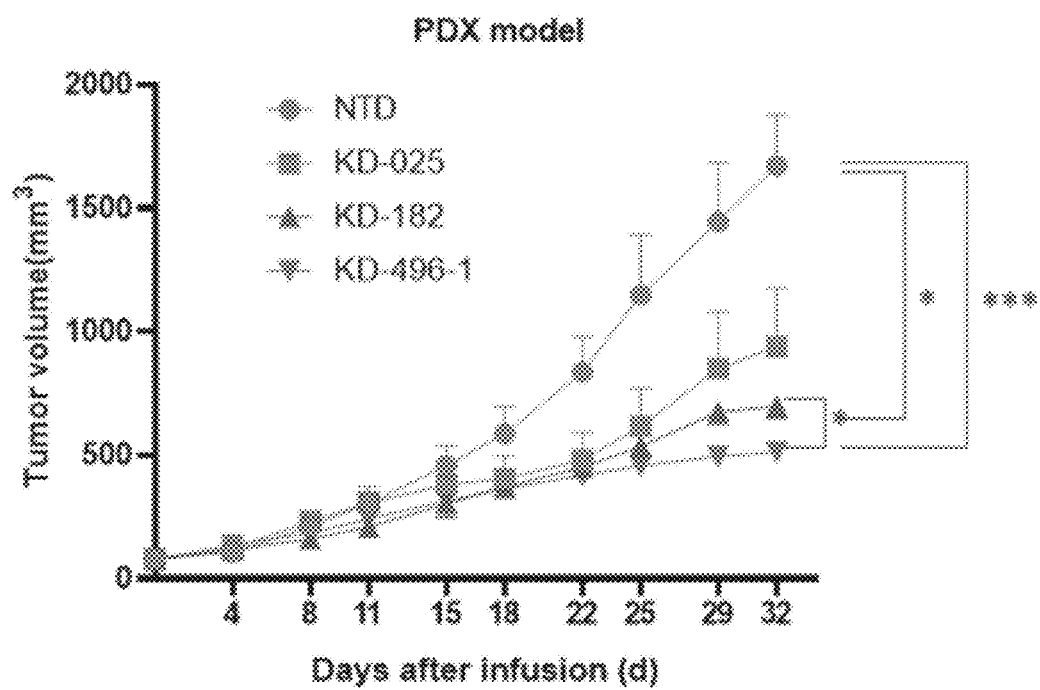

The human gastric cancer tissue was removed from the operation into a 15 ml centrifuge tube with 10 ml tissue preservation solution (L15 medium+1% PS) in the centrifuge tube. Take the sample back to the laboratory with an insulating bucket and an ice bag. After the sample arrives at the laboratory, the tissue is processed in the biosafety cabinet. The steps are as follows: take out the tissue in the centrifuge tube into a small dish (add L15 into the dish in advance); remove the fat and connective tissue at the edge of tumor tissue; and then cut the tumor tissue into uniform blocks, with the size of $2 \times 2 \times 2$ mm$^3$, and inoculated 2 pieces tissue samples at the left site by subcutaneous inoculation in immune deficient mice (B-NDG). As shown in FIG. 9A, immunohistochemical IHC results showed that the antigens of CLDN18A2 and NKG2DL (MICA and ULBP2/5/6) were highly expressed in gastric cancer tissues. When the tumor grew to about 50-100 mm$^3$, it was randomly divided into groups, n=5 in each group. CAR-T cells were prepared by infection according to the method of example 4, and CAR-T cells were injected into caudal vein, $1 \times 10^7$ cells/I00 μL. The tumor size of mice was measured twice a week. The results are shown in FIG. 9B, KD-025, KD-182 and KD-496-1 group have obvious inhibitory effect on tumors compared with the control group. In addition, the antitumor effect of KD-496-1 group was significantly better than that of KD-025 and KD-182 single groups.

Example 9. On-target Off-tumor Toxicities of KD-496-1 CAR-T Cells

Figure 10A:
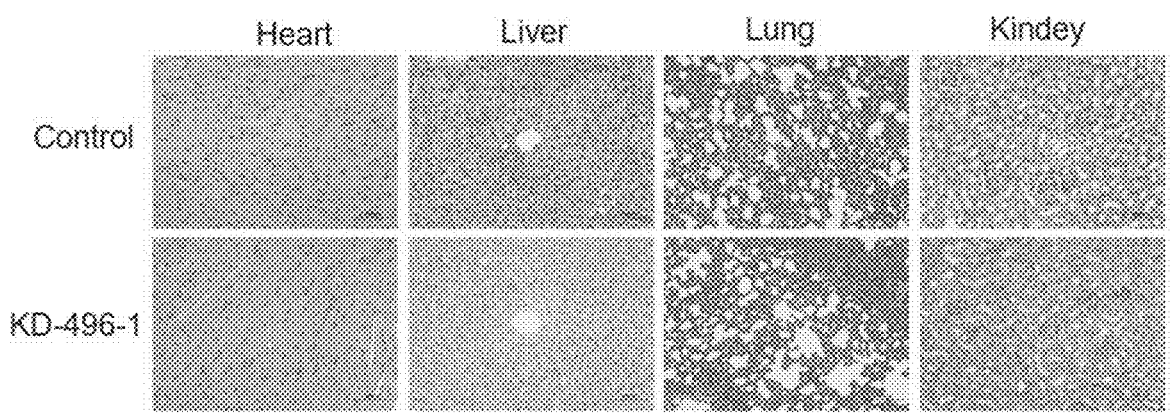
Figure 10B:
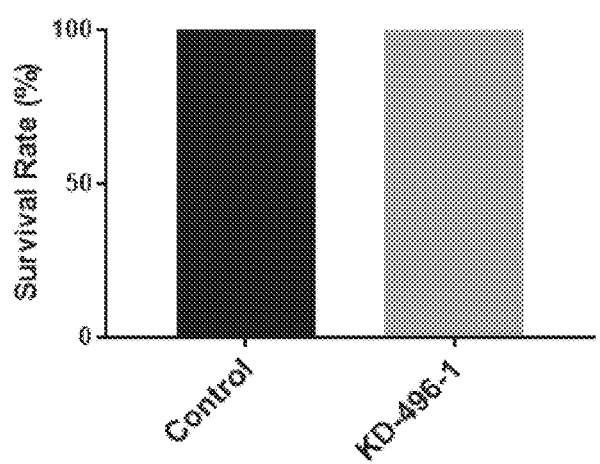

Firstly, the effector cells (KD-496-1 CAR-T cells) were prepared according to the method of Example 4, mice were treated with different dose of KD-496-1 CAR-T cells by intravenous injection. As shown in FIG. 10A, KD-496-1 CAR-T cells had no significant side effect on mice. And there was no negative effect on the life cycle of the mice as shown in FIG. 10B.

In conclusion, the viral vector or engineered immune cells which bi-specifically target the chimeric antigen receptor of human NKG2DL and CLDN18A2 can be applied to treat a variety of tumors, including gastric cancer, pancreatic cancer, liver cancer, brain cancer, lymph cancer, leukemia, colorectal cancer, lung cancer, or breast cancer. It can be understood that although the instruction is described in the embodiment, not each embodiment comprises only one independent technical proposal. This description of the instruction is only to be clear, and the skilled in this field should take as a whole, and the technical solutions in embodiments can also be suitably combined to forms other embodiments can be understood by technicians in the field.

A series of detailed descriptions listed are only specific instructions for the embodiment of the invention. They are not used to limit the scope of protection of the invention. The equivalent embodiment methods or changes that are not separated from the topic of the invention should be comprised in the scope of the protection of the invention.

What is claimed is:

1. An immune effector cell, comprising a bi-specific chimeric antigen receptor,
   wherein the bi-specific chimeric antigen receptor is expressed on a surface of the immune effector cell, and the bi-specific chimeric antigen receptor comprises extracellular binding regions, a hinge region, a transmembrane domain, and an intracellular signal domain,
   wherein the extracellular binding regions comprise proteins bi-specifically recognizing human CLDN18A2 and human NKG2DL, and the bi-specific chimeric antigen receptor comprises an amino acid sequence set forth in any one of SEQ ID NOS: 19-20.

2. A pharmaceutical composition, comprising the immune effector cell according to claim 1, and a pharmaceutically acceptable carrier.

3. The immune effector cell according to claim 1, wherein the immune effector cell is selected from the group consisting of a T lymphocyte, an NK cell, and a macrophage.

4. A method for treating a tumor in a patient in need thereof, comprising administering the immune effector cell according to claim 1 to the patient, wherein the tumor is a NKG2DL and CLDN18A2 positive tumor, thereby treating the tumor.

5. A bi-specific chimeric antigen receptor, comprising extracellular binding regions, a hinge region, a transmembrane domain, and an intracellular signal domain,
   wherein
   the extracellular binding regions comprise proteins bi-specifically recognizing human CLDN18A2 and human NKG2DL, and
   the bi-specific chimeric antigen receptor comprises an amino acid sequence set forth in any one of SEQ ID NOS: 19-20.

6. A method for preparing a genetically modified immune effector cell targeting human NKG2DL and human CLDN18A2, comprising: expressing the bi-specific chimeric antigen receptor according to claim 5 on a surface of an immune effector cell.

7. The method according to claim 6, wherein the immune effector cell is selected from the group consisting of a T lymphocyte, an NK cell, and a macrophage.

* * * * *

SEQUENCE LISTING

```
<160> NUMBER OF SEQ ID NOS: 22

<210> SEQ ID NO 1
<211> LENGTH: 21
<212> TYPE: PRT
<213> ORGANISM: Artificial Sequence
<220> FEATURE:
<223> OTHER INFORMATION: Leader sequence

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 2
```

Asp Ile Val Ile Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Tyr Pro Phe Thr Phe Gly Gly Gly Thr Lys Leu Glu Ile
            100                 105                 110

Lys Gly Gly Gly Gly Ser Gly Gly Gly Gly Ser Gly Gly Gly Gly Ser
            115                 120                 125

Glu Val Gln Leu Val Glu Ser Gly Gly Gly Val Val Gln Pro Gly Gly
        130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Arg Leu Glu Trp Val
                165                 170                 175

Ala Thr Phe Ser Ser Gly Gly Asp Tyr Thr Phe Tyr Pro Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Lys Leu Tyr Tyr Gly Asn Ser Met Asp Ser Trp Ser Gln Gly Leu
225                 230                 235                 240

Ser Val Thr Val Ser Ser
                245

<210> SEQ ID NO 3
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 3

Asp Ile Val Ile Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Gly Asn Gln Arg Asn Tyr Leu Thr Trp Tyr Leu Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Ala Tyr Tyr Tyr Pro Phe Thr Phe Gly Gly Gly Thr Lys Leu Glu Ile
            100                 105                 110

Lys Gly Gly Gly Ser Gly Gly Gly Ser Gly Gly Gly Ser
          115                 120                 125

Glu Val Gln Leu Leu Glu Ser Gly Gly Gly Leu Val Gln Pro Gly Gly
    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Asp Lys Arg Leu Glu Trp Val
                165                 170                 175

Ala Thr Phe Ser Ser Gly Gly Asp Tyr Thr Phe Tyr Pro Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Ile Tyr Tyr Cys
    210                 215                 220

Ala Lys Leu Tyr Tyr Gly Asn Ser Met Asp Ser Trp Ser Gln Gly Leu
225                 230                 235                 240

Ser Val Thr Val Ser Ser
                245

<210> SEQ ID NO 4
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 4

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Thr Tyr Ser Phe Pro Leu Thr Phe Gly Gln Gly Thr Lys Leu Glu Ile
            100                 105                 110

Lys Gly Gly Gly Gly Ser Gly Gly Gly Gly Ser Gly Gly Gly Gly Ser
        115                 120                 125

Asp Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Phe Ile Ser Ser Gly Ser His Thr Ile Tyr Tyr Ala Asp Ser Val
            180                 185                 190

Lys Gly Arg Phe Ser Ile Ser Arg Asp Asn Ala Lys Asn Thr Leu Phe
        195                 200                 205

Leu Gln Met Asn Ser Leu Arg Ala Glu Asp Thr Ala Val Tyr Tyr Cys
    210                 215                 220

```
Ala Arg Phe Gln Tyr Gly Asn Ser Phe Asp Tyr Trp Gly Gln Gly Thr
225                 230                 235                 240

Leu Val Thr Val Ser Ser
                245

<210> SEQ ID NO 5
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 5

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Thr Tyr Ser Phe Pro Leu Thr Phe Gly Gln Gly Thr Lys Leu Glu Ile
            100                 105                 110

Lys Gly Gly Gly Gly Ser Gly Gly Gly Gly Ser Gly Gly Gly Gly Ser
        115                 120                 125

Asp Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Phe Ile Ser Ser Gly Ser His Thr Ile Tyr Tyr Ala Asp Ser Val
            180                 185                 190

Lys Gly Arg Phe Ser Ile Ser Arg Asp Asn Ala Lys Asn Thr Leu Phe
        195                 200                 205

Leu Gln Met Asn Ser Leu Arg Ala Glu Asp Thr Ala Val Tyr Tyr Cys
    210                 215                 220

Ala Arg Phe Gln Tyr Gly Asn Ser Phe Asp Tyr Trp Gly Gln Gly Thr
225                 230                 235                 240

Leu Val Thr Val Ser Ser
                245

<210> SEQ ID NO 6
<211> LENGTH: 136
<212> TYPE: PRT
<213> ORGANISM: Artificial Sequence
<220> FEATURE:
<223> OTHER INFORMATION: NKG2D sequence

<400> SEQUENCE: 6

Ser Leu Phe Asn Gln Glu Val Gln Ile Pro Leu Thr Glu Ser Tyr Cys
1               5                   10                  15

Gly Pro Cys Pro Lys Asn Trp Ile Cys Tyr Lys Asn Asn Cys Tyr Gln
            20                  25                  30
```

Phe Phe Asp Glu Ser Lys Asn Trp Tyr Glu Ser Gln Ala Ser Cys Met
            35                  40                  45

Ser Gln Asn Ala Ser Leu Leu Lys Val Tyr Ser Lys Glu Asp Gln Asp
        50                  55                  60

Leu Leu Lys Leu Val Lys Ser Tyr His Trp Met Gly Leu Val His Ile
65                  70                  75                  80

Pro Thr Asn Gly Ser Trp Gln Trp Glu Asp Gly Ser Ile Leu Ser Pro
                85                  90                  95

Asn Leu Leu Thr Ile Ile Glu Met Gln Lys Gly Asp Cys Ala Leu Tyr
            100                 105                 110

Ala Ser Ser Phe Lys Gly Tyr Ile Glu Asn Cys Ser Thr Pro Asn Thr
            115                 120                 125

Tyr Ile Cys Met Gln Arg Thr Val
            130                 135

<210> SEQ ID NO 7
<211> LENGTH: 136
<212> TYPE: PRT
<213> ORGANISM: Artificial Sequence
<220> FEATURE:
<223> OTHER INFORMATION: NKG2D sequence

<400> SEQUENCE: 7

Ser Leu Phe Asn Lys Glu Val Gln Ile Pro Leu Thr Glu Ser Tyr Cys
1               5                   10                  15

Gly Pro Cys Pro Lys Asn Trp Ile Cys Tyr Lys Asn Asn Cys Tyr Gln
            20                  25                  30

Phe Phe Asp Glu Ser Lys Asn Trp Tyr Glu Ser Gln Ala Ser Cys Met
            35                  40                  45

Ser Gln Asn Ala Ser Leu Leu Lys Val Tyr Ser Lys Glu Asp Gln Asp
        50                  55                  60

Leu Leu Lys Leu Val Lys Ser Tyr His Trp Met Gly Leu Val His Ile
65                  70                  75                  80

Pro Thr Asn Gly Ser Trp Gln Trp Glu Asp Gly Ser Ile Leu Ser Pro
                85                  90                  95

Asn Leu Leu Thr Ile Ile Glu Met Gln Lys Gly Asp Cys Ala Leu Tyr
            100                 105                 110

Ala Ser Ser Phe Lys Gly Tyr Ile Glu Asn Cys Ser Thr Pro Asn Thr
            115                 120                 125

Tyr Ile Cys Met Gln Arg Thr Val
            130                 135

<210> SEQ ID NO 8
<211> LENGTH: 136
<212> TYPE: PRT
<213> ORGANISM: Artificial Sequence
<220> FEATURE:
<223> OTHER INFORMATION: NKG2D sequence

<400> SEQUENCE: 8

Ser Leu Phe Asn Gln Glu Val Gln Ile Pro Leu Thr Glu Ser Tyr Cys
1               5                   10                  15

Gly Pro Cys Pro Lys Asn Trp Ile Cys Tyr Lys Asn Asn Cys Tyr Gln
            20                  25                  30

Phe Phe Asp Glu Ser Lys Asn Trp Tyr Glu Ser Gln Ala Ser Cys Met
            35                  40                  45

Ser Gln Asn Ala Ser Leu Leu Lys Val Tyr Ser Lys Glu Asp Gln Asp

```
            50                  55                  60
Leu Leu Lys Leu Val Lys Ser Tyr His Trp Met Gly Leu Val His Ile
 65                  70                  75                  80

Pro Thr Asn Gly Ser Trp Gln Trp Glu Asp Gly Ser Ile Leu Ser Pro
                 85                  90                  95

Asn Leu Leu Thr Ile Ile Glu Met Lys Lys Gly Asp Cys Ala Leu Tyr
            100                 105                 110

Ala Ser Ser Phe Lys Gly Tyr Ile Glu Asn Cys Ser Thr Pro Asn Thr
            115                 120                 125

Tyr Ile Cys Met Lys Arg Thr Val
            130                 135

<210> SEQ ID NO 9
<211> LENGTH: 136
<212> TYPE: PRT
<213> ORGANISM: Artificial Sequence
<220> FEATURE:
<223> OTHER INFORMATION: NKG2D sequence

<400> SEQUENCE: 9

Ser Leu Phe Asn Gln Glu Val Gln Ile Pro Leu Thr Glu Ser Tyr Cys
  1               5                  10                  15

Gly Pro Cys Pro Lys Asn Trp Ile Cys Tyr Lys Asn Asn Cys Tyr Lys
                 20                  25                  30

Phe Phe Asp Glu Ser Lys Asn Trp Tyr Glu Ser Gln Ala Ser Cys Met
             35                  40                  45

Ser Gln Asn Ala Ser Leu Leu Lys Val Tyr Ser Lys Glu Asp Gln Asp
         50                  55                  60

Leu Leu Lys Leu Val Lys Ser Tyr His Trp Met Gly Leu Val His Ile
 65                  70                  75                  80

Pro Thr Asn Gly Ser Trp Gln Trp Glu Asp Gly Ser Ile Leu Ser Pro
                 85                  90                  95

Asn Leu Leu Thr Ile Ile Glu Met Gln Lys Gly Asp Cys Ala Leu Tyr
            100                 105                 110

Ala Ser Ser Phe Lys Gly Tyr Ile Glu Asn Cys Ser Thr Pro Asn Thr
            115                 120                 125

Tyr Ile Cys Met Gln Arg Thr Val
            130                 135

<210> SEQ ID NO 10
<211> LENGTH: 136
<212> TYPE: PRT
<213> ORGANISM: Artificial Sequence
<220> FEATURE:
<223> OTHER INFORMATION: NKG2D sequence

<400> SEQUENCE: 10

Ser Leu Phe Asn Lys Glu Val Lys Ile Pro Leu Thr Glu Ser Tyr Cys
  1               5                  10                  15

Gly Pro Cys Pro Lys Asn Trp Ile Cys Tyr Lys Asn Asn Cys Tyr Gln
                 20                  25                  30

Phe Phe Asp Glu Ser Lys Asn Trp Tyr Glu Ser Gln Ala Ser Cys Met
             35                  40                  45

Ser Gln Asn Ala Ser Leu Leu Lys Val Tyr Ser Lys Glu Asp Gln Asp
         50                  55                  60

Leu Leu Lys Leu Val Lys Ser Tyr His Trp Met Gly Leu Val His Ile
 65                  70                  75                  80
```

Pro Thr Asn Gly Ser Trp Gln Trp Glu Asp Gly Ser Ile Leu Ser Pro
                85                  90                  95

Asn Leu Leu Thr Ile Ile Glu Met Gln Lys Gly Asp Cys Ala Leu Tyr
            100                 105                 110

Ala Ser Ser Phe Lys Gly Tyr Ile Glu Asn Cys Ser Thr Pro Asn Thr
        115                 120                 125

Tyr Ile Cys Met Gln Arg Thr Val
    130                 135

<210> SEQ ID NO 11
<211> LENGTH: 136
<212> TYPE: PRT
<213> ORGANISM: Artificial Sequence
<220> FEATURE:
<223> OTHER INFORMATION: NKG2D sequence

<400> SEQUENCE: 11

Ser Leu Phe Asn Lys Glu Val Gln Ile Pro Leu Thr Glu Ser Tyr Cys
1               5                   10                  15

Gly Pro Cys Pro Lys Asn Trp Ile Cys Tyr Lys Asn Asn Cys Tyr Gln
            20                  25                  30

Phe Phe Asp Glu Ser Lys Asn Trp Tyr Glu Ser Gln Ala Ser Cys Met
        35                  40                  45

Ser Gln Asn Ala Ser Leu Leu Lys Val Tyr Ser Lys Glu Asp Gln Asp
    50                  55                  60

Leu Leu Lys Leu Val Lys Ser Tyr His Trp Met Gly Leu Val His Ile
65                  70                  75                  80

Pro Thr Asn Gly Ser Trp Gln Trp Glu Asp Gly Ser Ile Leu Ser Pro
                85                  90                  95

Asn Leu Leu Thr Ile Ile Glu Met Lys Lys Gly Asp Cys Ala Leu Tyr
            100                 105                 110

Ala Ser Ser Phe Lys Gly Tyr Ile Glu Asn Cys Ser Thr Pro Asn Thr
        115                 120                 125

Tyr Ile Cys Met Gln Arg Thr Val
    130                 135

<210> SEQ ID NO 12
<211> LENGTH: 45
<212> TYPE: PRT
<213> ORGANISM: Artificial Sequence
<220> FEATURE:
<223> OTHER INFORMATION: CD8 hinge region

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 13
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 13

Ile Tyr Ile Trp Ala Pro Leu Ala Gly Thr Cys Gly Val Leu Leu Leu

```
                                       1               5                  10                 15

Ser Leu Val Ile Thr Leu Tyr Cys
                20

<210> SEQ ID NO 14
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 14

Phe Trp Val Leu Val Val Val Gly Gly Val Leu Ala Cys Tyr Ser Leu
1               5                  10                 15

Leu Val Thr Val Ala Phe Ile Ile Phe Trp Val
                20                 25

<210> SEQ ID NO 15
<211> LENGTH: 42
<212> TYPE: PRT
<213> ORGANISM: Artificial Sequence
<220> FEATURE:
<223> OTHER INFORMATION: 4-1BB endodomain

<400> SEQUENCE: 15

Lys Arg Gly Arg Lys Lys Leu Leu Tyr Ile Phe Lys Gln Pro Phe Met
1               5                  10                 15

Arg Pro Val Gln Thr Thr Gln Glu Glu Asp Gly Cys Ser Cys Arg Phe
                20                 25                 30

Pro Glu Glu Glu Glu Gly Gly Cys Glu Leu
            35                 40

<210> SEQ ID NO 16
<211> LENGTH: 41
<212> TYPE: PRT
<213> ORGANISM: Artificial Sequence
<220> FEATURE:
<223> OTHER INFORMATION: CD28 co-stimulatory endodomain

<400> SEQUENCE: 16

Arg Ser Lys Arg Ser Arg Leu Leu His Ser Asp Tyr Met Asn Met Thr
1               5                  10                 15

Pro Arg Arg Pro Gly Pro Thr Arg Lys His Tyr Gln Pro Tyr Ala Pro
                20                 25                 30

Pro Arg Asp Phe Ala Ala Tyr Arg Ser
            35                 40

<210> SEQ ID NO 17
<211> LENGTH: 36
<212> TYPE: PRT
<213> ORGANISM: Artificial Sequence
<220> FEATURE:
<223> OTHER INFORMATION: OX40 endodomain

<400> SEQUENCE: 17

Arg Asp Gln Arg Leu Pro Pro Asp Ala His Lys Pro Pro Gly Gly Gly
1               5                  10                 15

Ser Phe Arg Thr Pro Ile Gln Glu Glu Gln Ala Asp Ala His Ser Thr
                20                 25                 30

Leu Ala Lys Ile
            35
```

```
<210> SEQ ID NO 18
<211> LENGTH: 112
<212> TYPE: PRT
<213> ORGANISM: Artificial Sequence
<220> FEATURE:
<223> OTHER INFORMATION: CD3 zeta endodomain

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 654
<212> TYPE: PRT
<213> ORGANISM: Artificial Sequence
<220> FEATURE:
<223> OTHER INFORMATION: chimeric antigen receptor protein KD-496-1

<400> SEQUENCE: 19

Met Ala Leu Pro Val Thr Ala Leu Leu Leu Pro Leu Ala Leu Leu Leu
1               5                   10                  15

His Ala Ala Arg Pro Asp Ile Val Ile Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Leu Leu Asn Ser Gly Asn Gln Arg Asn Tyr Leu Thr Trp Tyr Gln
    50                  55                  60

Gln Lys Pro Gly Gln Pro Pro Lys Leu Leu Phe Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Asn Ala Tyr Tyr Pro Phe Thr Phe Gly Gly Gly
        115                 120                 125

Thr Lys Leu Glu Ile Lys Gly Gly Gly Ser Gly Gly Gly Ser
    130                 135                 140

Gly Gly Gly Gly Ser Glu Val Gln Leu Val Glu Ser Gly Gly Gly Val
145                 150                 155                 160

Val Gln Pro Gly Gly Ser Leu Arg Leu Ser Cys Ala Ala Ser Gly Phe
                165                 170                 175

Thr Phe Ser Lys Phe Gly Met Ser Trp Val Arg Gln Ala Pro Gly Lys
            180                 185                 190

Arg Leu Glu Trp Val Ala Thr Phe Ser Ser Gly Gly Asp Tyr Thr Phe
        195                 200                 205
```

-continued

```
Tyr Pro Asp Ser Val Lys Gly Arg Phe Thr Ile Ser Arg Asp Asn Ser
    210                 215                 220
Lys Asn Thr Leu Tyr Leu Gln Met Asn Ser Leu Arg Ala Glu Asp Thr
225                 230                 235                 240
Ala Val Tyr Tyr Cys Ala Lys Leu Tyr Tyr Gly Asn Ser Met Asp Ser
                245                 250                 255
Trp Ser Gln Gly Leu Ser Val Thr Val Ser Ser Gly Gly Gly Gly Ser
            260                 265                 270
Gly Gly Gly Ser Gly Gly Gly Gly Ser Gly Gly Gly Gly Ser Gly
        275                 280                 285
Gly Gly Gly Ser Ser Leu Phe Asn Gln Glu Val Gln Ile Pro Leu Thr
    290                 295                 300
Glu Ser Tyr Cys Gly Pro Cys Pro Lys Asn Trp Ile Cys Tyr Lys Asn
305                 310                 315                 320
Asn Cys Tyr Gln Phe Phe Asp Glu Ser Lys Asn Trp Tyr Glu Ser Gln
                325                 330                 335
Ala Ser Cys Met Ser Gln Asn Ala Ser Leu Leu Lys Val Tyr Ser Lys
            340                 345                 350
Glu Asp Gln Asp Leu Leu Lys Leu Val Lys Ser Tyr His Trp Met Gly
        355                 360                 365
Leu Val His Ile Pro Thr Asn Gly Ser Trp Gln Trp Glu Asp Gly Ser
    370                 375                 380
Ile Leu Ser Pro Asn Leu Leu Thr Ile Ile Glu Met Gln Lys Gly Asp
385                 390                 395                 400
Cys Ala Leu Tyr Ala Ser Ser Phe Lys Gly Tyr Ile Glu Asn Cys Ser
                405                 410                 415
Thr Pro Asn Thr Tyr Ile Cys Met Gln Arg Thr Val Ala Ala Ala Thr
            420                 425                 430
Thr Thr Pro Ala Pro Arg Pro Pro Thr Pro Ala Pro Thr Ile Ala Ser
        435                 440                 445
Gln Pro Leu Ser Leu Arg Pro Glu Ala Cys Arg Pro Ala Ala Gly Gly
    450                 455                 460
Ala Val His Thr Arg Gly Leu Asp Phe Ala Cys Asp Ile Tyr Ile Trp
465                 470                 475                 480
Ala Pro Leu Ala Gly Thr Cys Gly Val Leu Leu Leu Ser Leu Val Ile
                485                 490                 495
Thr Leu Tyr Cys Lys Arg Gly Arg Lys Lys Leu Leu Tyr Ile Phe Lys
            500                 505                 510
Gln Pro Phe Met Arg Pro Val Gln Thr Thr Gln Glu Glu Asp Gly Cys
        515                 520                 525
Ser Cys Arg Phe Pro Glu Glu Glu Gly Gly Cys Glu Leu Arg Val
    530                 535                 540
Lys Phe Ser Arg Ser Ala Asp Ala Pro Ala Tyr Gln Gln Gly Gln Asn
545                 550                 555                 560
Gln Leu Tyr Asn Glu Leu Asn Leu Gly Arg Arg Glu Glu Tyr Asp Val
                565                 570                 575
Leu Asp Lys Arg Arg Gly Arg Asp Pro Glu Met Gly Gly Lys Pro Arg
            580                 585                 590
Arg Lys Asn Pro Gln Glu Gly Leu Tyr Asn Glu Leu Gln Lys Asp Lys
        595                 600                 605
Met Ala Glu Ala Tyr Ser Glu Ile Gly Met Lys Gly Glu Arg Arg Arg
    610                 615                 620
Gly Lys Gly His Asp Gly Leu Tyr Gln Gly Leu Ser Thr Ala Thr Lys
```

```
                625                 630                 635                 640

Asp Thr Tyr Asp Ala Leu His Met Gln Ala Leu Pro Pro Arg
                            645                 650

<210> SEQ ID NO 20
<211> LENGTH: 654
<212> TYPE: PRT
<213> ORGANISM: Artificial Sequence
<220> FEATURE:
<223> OTHER INFORMATION: chimeric antigen receptor protein KD-496-2

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Val Ile Thr Gln Ser Pro Leu Ser Leu
                20                  25                  30

Pro Val Thr Pro Gly Glu Pro Ala Ser Ile Ser Cys Lys Ser Ser Gln
            35                  40                  45

Ser Leu Leu Asn Ser Gly Asn Gln Arg Asn Tyr Leu Thr Trp Tyr Leu
        50                  55                  60

Gln Lys Pro Gly Gln Pro Pro Lys Leu Leu Phe Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Gln Asn Ala Tyr Tyr Pro Phe Thr Phe Gly Gly Gly
        115                 120                 125

Thr Lys Leu Glu Ile Lys Gly Gly Gly Ser Gly Gly Gly Ser
130                 135                 140

Gly Gly Gly Gly Ser Glu Val Gln Leu Leu Glu Ser Gly Gly Gly Leu
145                 150                 155                 160

Val Gln Pro Gly Gly Ser Leu Arg Leu Ser Cys Ala Ala Ser Gly Phe
                165                 170                 175

Thr Phe Ser Lys Phe Gly Met Ser Trp Val Arg Gln Ala Pro Asp Lys
            180                 185                 190

Arg Leu Glu Trp Val Ala Thr Phe Ser Ser Gly Gly Asp Tyr Thr Phe
        195                 200                 205

Tyr Pro Asp Ser Val Lys Gly Arg Phe Thr Ile Ser Arg Asp Asn Ser
    210                 215                 220

Lys Asn Thr Leu Tyr Leu Gln Met Asn Ser Leu Arg Ala Glu Asp Thr
225                 230                 235                 240

Ala Ile Tyr Tyr Cys Ala Lys Leu Tyr Tyr Gly Asn Ser Met Asp Ser
                245                 250                 255

Trp Ser Gln Gly Leu Ser Val Thr Val Ser Ser Gly Gly Gly Gly Ser
            260                 265                 270

Gly Gly Gly Gly Ser Gly Gly Gly Ser Gly Gly Gly Gly Ser Gly
        275                 280                 285

Gly Gly Gly Ser Ser Leu Phe Asn Gln Glu Val Gln Ile Pro Leu Thr
    290                 295                 300

Glu Ser Tyr Cys Gly Pro Cys Pro Lys Asn Trp Ile Cys Tyr Lys Asn
305                 310                 315                 320

Asn Cys Tyr Gln Phe Phe Asp Glu Ser Lys Asn Trp Tyr Glu Ser Gln
                325                 330                 335

Ala Ser Cys Met Ser Gln Asn Ala Ser Leu Leu Lys Val Tyr Ser Lys
```

```
            340                 345                 350
Glu Asp Gln Asp Leu Leu Lys Leu Val Lys Ser Tyr His Trp Met Gly
        355                 360                 365
Leu Val His Ile Pro Thr Asn Gly Ser Trp Gln Trp Glu Asp Gly Ser
    370                 375                 380
Ile Leu Ser Pro Asn Leu Leu Thr Ile Ile Glu Met Gln Lys Gly Asp
385                 390                 395                 400
Cys Ala Leu Tyr Ala Ser Ser Phe Lys Gly Tyr Ile Glu Asn Cys Ser
            405                 410                 415
Thr Pro Asn Thr Tyr Ile Cys Met Gln Arg Thr Val Ala Ala Ala Thr
        420                 425                 430
Thr Thr Pro Ala Pro Arg Pro Pro Thr Pro Ala Pro Thr Ile Ala Ser
    435                 440                 445
Gln Pro Leu Ser Leu Arg Pro Glu Ala Cys Arg Pro Ala Ala Gly Gly
        450                 455                 460
Ala Val His Thr Arg Gly Leu Asp Phe Ala Cys Asp Ile Tyr Ile Trp
465                 470                 475                 480
Ala Pro Leu Ala Gly Thr Cys Gly Val Leu Leu Leu Ser Leu Val Ile
            485                 490                 495
Thr Leu Tyr Cys Lys Arg Gly Arg Lys Lys Leu Leu Tyr Ile Phe Lys
        500                 505                 510
Gln Pro Phe Met Arg Pro Val Gln Thr Thr Gln Glu Glu Asp Gly Cys
        515                 520                 525
Ser Cys Arg Phe Pro Glu Glu Glu Glu Gly Gly Cys Glu Leu Arg Val
    530                 535                 540
Lys Phe Ser Arg Ser Ala Asp Ala Pro Ala Tyr Gln Gln Gly Gln Asn
545                 550                 555                 560
Gln Leu Tyr Asn Glu Leu Asn Leu Gly Arg Arg Glu Glu Tyr Asp Val
            565                 570                 575
Leu Asp Lys Arg Arg Gly Arg Asp Pro Glu Met Gly Gly Lys Pro Arg
        580                 585                 590
Arg Lys Asn Pro Gln Glu Gly Leu Tyr Asn Glu Leu Gln Lys Asp Lys
        595                 600                 605
Met Ala Glu Ala Tyr Ser Glu Ile Gly Met Lys Gly Glu Arg Arg Arg
    610                 615                 620
Gly Lys Gly His Asp Gly Leu Tyr Gln Gly Leu Ser Thr Ala Thr Lys
625                 630                 635                 640
Asp Thr Tyr Asp Ala Leu His Met Gln Ala Leu Pro Pro Arg
            645                 650

<210> SEQ ID NO 21
<211> LENGTH: 1962
<212> TYPE: DNA
<213> ORGANISM: Artificial Sequence
<220> FEATURE:
<223> OTHER INFORMATION: chimeric antigen receptor protein KD-496-1

<400> SEQUENCE: 21
atggccctgc cgtcaccgc tctgctgctg cccttgctc tgcttcttca tgcagcaagg      60
ccggatatcg ttataaccca atctcccgac tcattggcag tcagtttggg cgaacgggcg    120
actattaact gtaaatcatc acagtctttg ctcaactcag caatcagag aaattacctg    180 acttggtatc aacagaagcc cgggcaaccg ccaaaactgt tgttttattg ggcttcaaca    240
cgggaaagtg gggtgcctga tcggtttaca gggagcggat ccggcaccga ttttactttg    300
```

-continued

```
acaatctctt cactgcaagc cgaggacgta gcggtttact attgtcaaaa tgcctattat    360
tacccattta ccttcggagg cgggacaaaa cttgaaataa aggtggcgg aggctctggc    420 ggcgggggct caggggtgg tggttctgag gttcaacttg tagagagtgg aggaggagtt    480
gtacaaccgg gggcagtct tagactttct tgcgctgcat ctgggtttac attctctaag    540
tttggaatga gttgggtgag acaagcgccc ggtaagcgcc ttgagtgggt agcaactttt    600
agctcaggtg gtgactacac cttctaccca gactccgtga agggtcggtt caccattagc    660
cgagataact caaaaaacac gctttacctg caaatgaaca gtctgcgagc tgaggatacg    720
gcggtatatt actgtgcaaa gttgtattat ggaaatagca tggattcctg gagccagggt    780
ctctctgtga cagtttctag tggaggaggg ggttccgggg gaggcggctc tggcggcgga    840
gggagtggcg ggggggttc aggggtgga ggaagctctc tgttcaacca agaggtgcag    900
ataccactta ccgaatcata ttgtggcccc tgcccaaaga actggatatg ttacaaaaat    960
aattgctacc agttttttcga cgagtccaag aattggtatg aatcacaagc cagctgcatg   1020
tcccaaaatg cgtcattgtt gaaggtatat tctaaggagg accaagatt gttgaagttg   1080 gttaaatcct atcattggat ggggttggtc catataccta caaatggttc atggcagtgg   1140
gaagatggat ctatactgag cccaaatctt ctgacaataa ttgaaatgca aaaaggcgat   1200
tgtgcccttt acgctagtag cttcaaaggt tatattgaga actgtagcac accgaacact   1260
tatatctgta tgcagagaac ggttgccgct gcaaccacga cgccagcgcc gcgaccacca   1320
acaccggcgc ccaccatcgc gtcgcagccc ctgtccctgc gcccagaggc gtgccggcca   1380
gcggcggggg gcgcagtgca cacgagggg ctggacttcg cctgtgatat ctacatctgg   1440
gcgcccttgg ccgggacttg tggggtcctt ctcctgtcac tggttatcac cctttactgc   1500
aaacggggca gaaagaaact cctgtatata ttcaaacaac catttatgag accagtacaa   1560
actactcaag aggaagatgg ctgtagctgc cgatttccag aagaagaaga aggaggatgt   1620
gaactgagag tgaagttcag caggagcgca acgccccccg cgtaccagca gggccagaac   1680
cagctctata cgagctcaa tctaggacga agagaggagt acgatgtttt ggacaagaga   1740
cgtggccggg accctgagat gggggaaag ccgagaagga agaaccctca ggaaggcctg   1800
tacaatgaac tgcagaaaga taagatggcg gaggcctaca gtgagattgg gatgaaaggc   1860
gagcgccgga ggggcaaggg gcacgatggc ctttaccagg gtctcagtac agccaccaag   1920
gacacctacg acgcccttca catgcaggcc ctgccccctc gc                      1962
```

<210> SEQ ID NO 22
<211> LENGTH: 1962
<212> TYPE: DNA
<213> ORGANISM: Artificial Sequence
<220> FEATURE:
<223> OTHER INFORMATION: chimeric antigen receptor protein KD-496-2

<400> SEQUENCE: 22

```
atggccctgc ccgtcaccgc tctgctgctg ccccttgctc tgcttcttca tgcagcaagg     60
ccggacatag tcataacaca atctccgctt agcttgccgg tcactcctgg cgaaccagcc    120
tctatcagtt gtaaaagctc acaatcactg ctcaatagcg gaaccagcg gaactatttg    180 acatggtacc tccaaaaacc tggtcaacct ccaaagctgc tgtttactg ggcctcaacg    240 cgggagtcag ggttcctga tcggtttact ggttcaggca gcggtacaga ttttacgctg    300
aaaataagca gggttgaggc agaagatgtc ggtgtctatt actgtcagaa cgcatattac    360 tacccgtttta cctttggtgg cggtacaaag ctggaaatca aaggcggggg cggaagcgga    420
```

-continued

```
ggtggtggtt caggtggagg cggttccgaa gtgcagcttc ttgaaagtgg tggtgggttg    480
gtacaaccag gaggcagtct cagactgtcc tgtgccgctt ccggcttcac gttctctaag    540
tttggaatgt catgggtacg acaggcaccc gataagcgcc tcgaatgggt cgcaactttt    600
tccagcggtg gtgattacac gttctatcca gattcagtca aaggccggtt tacgatctcc    660
cgagataaca gtaagaatac actgtatctt caaatgaatt cacttcgggc agaagatacc    720
gcgatttatt attgcgctaa actttactac gggaactcta tggattcctg gagtcaaggc    780
ttgagtgtta ctgtatcaag tggaggaggg ggttccgggg gaggcggctc tggcggcgga    840
gggagtggcg ggggggttc aggggtgga ggaagctctc tgttcaacca agaggtgcag    900
ataccactta ccgaatcata ttgtggcccc tgcccaaaga actggatatg ttacaaaaat    960
aattgctacc agttttcga cgagtccaag aattggtatg aatcacaagc cagctgcatg   1020
tcccaaaatg cgtcattgtt gaaggtatat tctaaggagg accaagattt gttgaagttg   1080
gttaaatcct atcattggat ggggttggtc catataccta caaatggttc atggcagtgg   1140
gaagatggat ctatactgag cccaaatctt ctgacaataa ttgaaatgca aaaaggcgat   1200
tgtgcccttt acgctagtag cttcaaaggt tatattgaga actgtagcac accgaacact   1260
tatatctgta tgcagagaac ggttgccgct gcaaccacga cgccagcgcc gcgaccacca   1320
acaccggcgc ccaccatcgc gtcgcagccc ctgtccctgc gcccagaggc gtgccggcca   1380
gcggcggggg gcgcagtgca cacgaggggg ctggacttcg cctgtgatat ctacatctgg   1440
gcgcccttgg ccgggacttg tggggtcctt ctcctgtcac tggttatcac cctttactgc   1500
aaacggggca gaaagaaact cctgtatata ttcaaacaac catttatgag accagtacaa   1560
actactcaag aggaagatgg ctgtagctgc cgatttccag aagaagaaga aggaggatgt   1620
gaactgagag tgaagttcag caggagcgca gacgcccccg cgtaccagca gggccagaac   1680
cagctctata acgagctcaa tctaggacga agagaggagt acgatgtttt ggacaagaga   1740
cgtggccggg accctgagat gggggaaag ccgagaagga agaaccctca ggaaggcctg   1800
tacaatgaac tgcagaaaga taagatggcg gaggcctaca gtgagattgg gatgaaaggc   1860
gagcgccgga ggggcaaggg gcacgatggc ctttaccagg gtctcagtac agccaccaag   1920
gacacctacg acgcccttca catgcaggcc ctgccccctc gc                      1962
```